US007947253B2

(12) United States Patent
Ziv et al.

(10) Patent No.: US 7,947,253 B2
(45) Date of Patent: *May 24, 2011

(54) PERTURBED MEMBRANE-BINDING COMPOUNDS AND METHODS OF USING THE SAME

(75) Inventors: Ilan Ziv, Kfar Saba (IL); Anat Shirvan, Herzliya (IL)

(73) Assignee: Aposense Ltd., Petach-Tikva (IL)

( * ) Notice: Subject to any disclaimer, the term of this patent is extended or adjusted under 35 U.S.C. 154(b) by 1312 days.

This patent is subject to a terminal disclaimer.

(21) Appl. No.: 10/585,928

(22) PCT Filed: Jan. 16, 2005

(86) PCT No.: PCT/IL2005/000055
§ 371 (c)(1),
(2), (4) Date: Jul. 13, 2006

(87) PCT Pub. No.: WO2005/067388
PCT Pub. Date: Jul. 28, 2005

(65) Prior Publication Data
US 2008/0279774 A1 Nov. 13, 2008

Related U.S. Application Data

(63) Continuation-in-part of application No. 10/799,586, filed on Mar. 15, 2004, now Pat. No. 7,270,799.

(60) Provisional application No. 60/536,493, filed on Jan. 15, 2004, provisional application No. 60/537,289, filed on Jan. 20, 2004.

(51) Int. Cl.
*A61K 51/00* (2006.01)
*A61K 49/04* (2006.01)

(52) U.S. Cl. ..................... 424/1.11; 424/9.364; 424/9.4

(58) Field of Classification Search .............. 424/9.364, 424/9.4
See application file for complete search history.

(56) References Cited

U.S. PATENT DOCUMENTS

| 4,187,381 | A  | * | 2/1980  | Holland |             |
|-----------|----|---|---------|---------|-------------|
| 4,578,503 | A  |   | 3/1986  | Ishikawa et al. |     |
| 7,270,799 | B2 | * | 9/2007  | Ziv et al. | ......... 424/1.11 |
| 7,670,590 | B2 | * | 3/2010  | Ziv et al. | ......... 424/1.11 |

FOREIGN PATENT DOCUMENTS

| FR | 2 197 873    | * | 3/1974 |
| FR | 2 274 600    | * | 1/1976 |
| GB | 1401579      |   | 7/1975 |
| JP | 57 085338    | * | 5/1982 |
| WO | WO 97/00848  | * | 1/1997 |
| WO | WO 02/46147  |   | 6/2002 |

OTHER PUBLICATIONS

Gershon H. Organic fluorine compounds.II., Journal of Medicinal Chemistry 1967, p. 186-188, vol. 10, No. 2, American Chemical Society.
Bevers, E.M., et al., Lipid translocation across the plasma membrane of mammalian cells, Biochimica et Biophysica Acta 1439 (1999) 317-330 Elsevier.
Bombeli, T., et al, Apoptotic Vascular Endothelial Cells Become Procoagulant, Blood, Apr. 1, 1997, pp. 2429-2442, vol. 89, No. 7. American Society of Hematology, Washington DC.
Bratton, D.L., et al, Appearance of Phosphatidylserine on Apoptotic Cells Requires Calcium-mediated Nonspecific Flip-Flop and is Enhanced by Loss of the Aminophospholipid Translocase, The Journal of Biological Chemistry, Oct. 17, 1997, pp. 26159-26165, vol. 272, No. 42, The American Society for Biochemistry and Molecular Biology, Inc.
Bursch, W., et al, Cell death by apoptosis and its protective role against disease, Trends Pharmacol Sci. Jun. 1992; 13(6):245-51.
Kockx M.M., et al, Apoptosis in atherosclerosis: beneficial or detrimental? Cardiovasc. Res., 2000, 736-746, vo. 45, Elsevier.
Mallat, Z., et al, Colocalization of CPP-32 With Apoptotic Cells in Human Atherosclerotic Plaques Circulation, 1997; 424-428 vol. 96, American Heart Association, Inc.
Martin, S., et al, Early Redistribution of Plasma Membrane Phosphatidylserine Is a General Feature of Apoptosis Regardless of the Initiating Stimulus: Inhibition by Overexpression of Bcl-2 and Abl, J. Exp.Med, Nov. 1995, 1545 vol. 182.
Pugsley, W., et al The impact of microemboli during cardiopulmonary bypass on neuropsychological functioning, Stroke, 1994, 1393-1399, vol. 25, American Heart Association.
Sims, P.J., et al, Unraveling the Mysteries of Phospholipid Scrambling Thromb. Haemost, 2001; p. 266-75, vol. 86, Schattauer GmbH, Stuttgart.
Stary, H.C., et al., A Definition of Advanced Types of Atherosclerotic Lesions and a Histological Classification of Atherosclerosis, Circulation, 1995, p. 1355-1374, vol. 92, American Heart Association, Inc.
Van Den Eijnde, S.M., et al, Phosphatidylserine plasma membrane asymmetry in vivo: a pancellular phenomenon which alters during apoptosis, Cell Death Differentiation, 1997, p. 311-316, vol. 4, Stockton Press.
JoAnne Stubbe et al. Are Carboxylations Involving Biotin Concerted or Nonconcerted? The Journal of Biological Chemistry vol. 25, No. 1 Issue of Jan. 10, pp. 236-242, 1980. Graduate Dept. of Biochemistry, Brandies University, Waltham, MA, USA & Dept. of Pharmacology, Yael University, New Haven, Connecticut, USA.
Peggy L. Olive et al. Characterization of the Uptake and Toxicity of a Fluorescent Thiol Reagent Cytometry by the Society for Analytical Cytology pp. 349-353 vol. 3, No. 5, Jul. 12, 1982 The John Hopkins Oncology Center, Section of Radiobiology, Baltimore, Maryland USA & Dept. of Radiology, Case Western Reserve University, Cleveland, Ohio, USA.
International Search Report for PCT/IL05/00055 mailed Jul. 21, 2005.

* cited by examiner

*Primary Examiner* — Michael G. Hartley
*Assistant Examiner* — Jagadishwar R Samala
(74) *Attorney, Agent, or Firm* — Pearl Cohen Zedek Latzer, LLP

(57) ABSTRACT

The present invention relates to compounds that selectively bind to cells undergoing perturbations and alterations of their normal plasma membrane organization, such as cells undergoing apoptosis or activated platelets. The invention further provides methods for utilizing said compounds in medical practice, for diagnostic and therapeutic purposes.

19 Claims, 13 Drawing Sheets

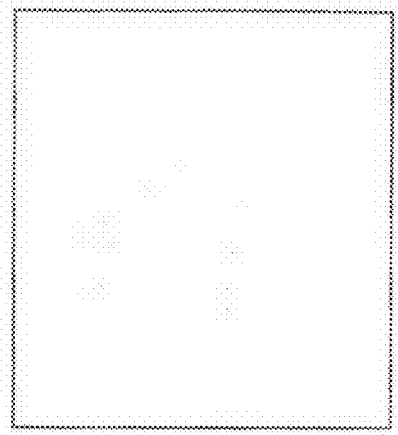
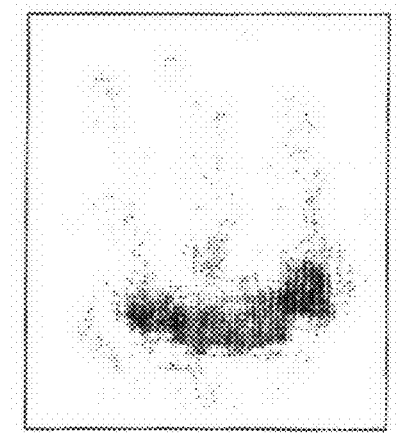
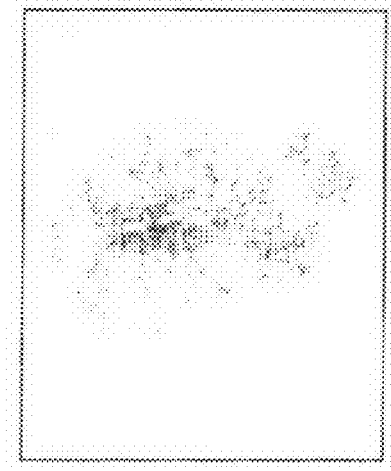
FIG. 5A
FIG. 5C
FIG. 5B

|  | Control | Doxo (2x20 mg/kg) |
|---|---|---|
| Tumor/Kidney | 0.86 | 0.59 |
| Tumor/Heart | 1.07 | 5.69 |
| Tumor/Liver | 0.88 | 4.68 |
| Tumor/Muscle | 1.61 | 8.66 |
| Tumor/Fast tissue | 6.60 | 5.20 |
| Tumor/Spleen | 2.42 | 3.86 |
| Tumor/Lung | 1.07 | 2.52 |
| Tumor/Blood | 1.43 | 3.50 |
| Tumor/Small intestine | 1.18 | 2.26 |

| | | |
|---|---|---|
| Tumor | 0.07 | 1.28 |

FIG. 7

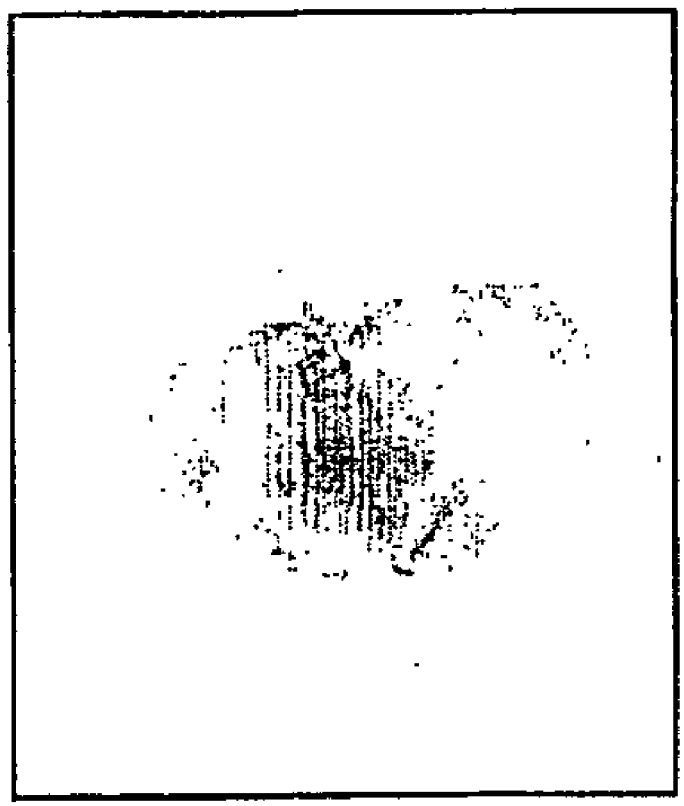
FIG. 10A Ischemic kidney
FIG. 10B Contralateral side kidney

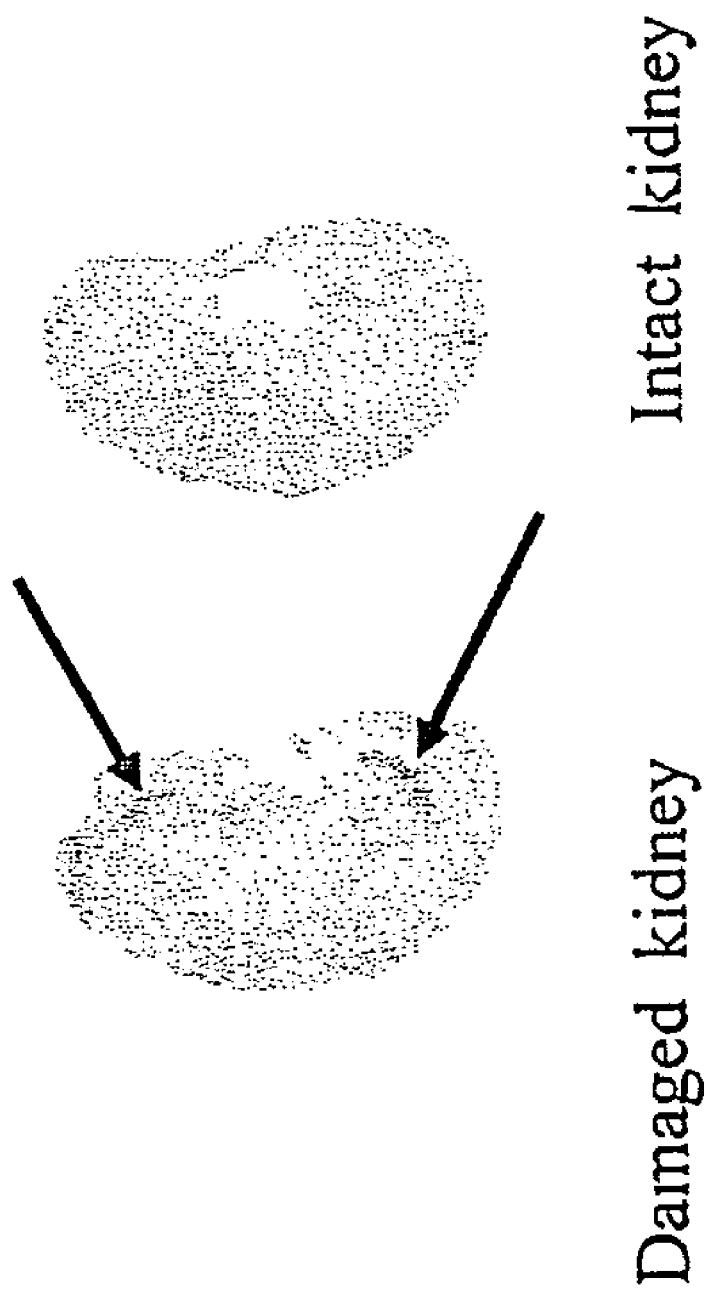
FIG. 11A Damaged kidney
FIG. 11B Intact kidney

PERTURBED MEMBRANE-BINDING COMPOUNDS AND METHODS OF USING THE SAME

CROSS-REFERENCE TO RELATED APPLICATIONS

This application is a National Phase application of PCT International Application No. PCT/IL2005/000055, International Filing Date: Jan. 16, 2005, claiming priority from U.S. Provisional Patent Application Ser. No. 60/536,493, entitled "PERTURBED MEMBRANE-BINDING COMPOUNDS" filed Jan. 15, 2004, U.S. Provisional Patent Application Ser. No. 60/537,289, entitled "PERTURBED MEMBRANE-BINDING COMPOUNDS" filed Jan. 20, 2004 and is a Continuation in Part of U.S. patent application Ser. No. 10/799,586, entitled "PERTURBED MEMBRANE-BINDING COMPOUNDS AND METHODS OF USING THE SAME" filed Mar. 15, 2004 now U.S. Pat. No. 7,270,799, all of which are incorporated by reference in their entirety.

FIELD OF THE INVENTION

The invention relates to compounds that selectively bind to cells undergoing perturbations and alterations of their normal plasma membrane organization, i.e., cells undergoing cell death, apoptotic cells or activated platelets. The invention further provides methods for utilizing the compounds in medical practice, for diagnostic and therapeutic purposes.

BACKGROUND OF THE INVENTION

The plasma membrane (outer membrane) of intact eukaryotic cells is characterized by a highly organized structure. This high level of membrane organization is determined, among others, by the molecular structure of the specific lipids constituting the membrane; the ratio between the various lipid species from which the membrane is composed; the distribution of the phospholipids between the outer and inner leaflets of the membrane; and by the membrane protein constituents.

While maintenance of the high level of plasma membrane organization is fundamental to normal cell physiology, substantial perturbations and alterations of the normal organization of the cell plasma membrane (PNOM) occur in numerous physiological and pathological conditions, and are characterizing a plurality of diseases. Such alterations and perturbations may be evident both at the morphological level (membrane blebbing observed in cells undergoing apoptosis) and at the molecular level. PNOM includes, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and reciprocal movement of sphingomyelin (SM) and phosphatidylcholine (PC) from the outer leaflet to the inner leaflet of the membrane. This redistribution is referred herein as loss of cell Membrane lipid asymmetry (CMLA). In addition to CMLA loss, PNOM is also often associated with reduction in the level of packing of membrane pbospholipids and an increase in membrane fluidity.

These alterations play an important role in rendering the cell surface a catalytic platform for the assembly of several clotting factor complexes, such as the tenase and prothrombinase protein complexes. Accordingly, platelet activation is associated with the platelet membrane undergoing PNOM, and these alterations constitute an important factor in normal blood coagulation, as well as in the initiation and/or propagation of abnormal, excessive blood clotting in numerous disorders. These disorders include, among others, arterial or venous thrombosis or thrombo-embolism [e.g., cerebral stroke, myocardial infarction, deep vein thrombosis (DVT), disseminated intravascular coagulation (DIC), thrombotic thrombocytopenic purpura, etc.], unstable atherosclerotic plaques, sickle cell disease, beta-thalassemia, anti-phospholipid antibody syndrome [among others in systemic lupus erythematosus (SLE)], and disorders associated with shedding of membrane microparticles, e.g., neurological dysfunction in association with cardiopulmonary bypass.

Apoptosis is another major situation in which alterations/perturbations of cell membrane tale place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages. PNOM is a universal phenomenon of apoptosis, it occurs early in the apoptotic cascade, probably at the point of cell commitment to the death process, and has also been shown to be an important factor in the recognition and removal of apoptotic cells by macrophages.

A strong correlation has been recently drawn between PNOM and the potent procoagulant activity of apoptotic cells. PNOM in apoptotic endothelial cells, such as those occurring in atherosclerotic plaques, probably plays an important role in the pathogenesis of thrombotic vascular disorders.

Since apoptosis or thrombosis each has an important role in the majority of medical disorders, it is desirable to have tools for detection of these biological processes and targeting of associated cells. Compounds for selective binding to PNOM-membranes, potentially also performing subsequent entry into these cells having such PNOM-membranes (PNOM-cells), may therefore serve as an important tool for detecting and targeting of imaging agents or drugs to cells undergoing damage or death process, especially by apoptosis, or to platelets undergoing activation.

SUMMARY OF THE INVENTION

In an aspect of the invention, there are provided compounds that can selectively bind to cells undergoing perturbation of their normal organization of the plasma membrane (PNOM-cells), while binding to a lesser degree to cells, which maintain the normal organization of their plasma membrane, and which are defined hereto as "normal cells". The PNOM-cells are, in an embodiment of the invention, cells undergoing a death process. In an embodiment of the invention the cells are apoptotic cells, and in another embodiment, the cells may be activated platelets. The invention further relates to methods of detecting PNOM-cells by using these compounds, which selectively bind to the PNOM-cells. In another embodiment of the invention, compounds are provided, represented by structures set forth in formulae I-XIV.

The term "perturbed membrane-binding compound" (PMBC) refers to a compound that selectively targets PNOM-cells, while binding to a lesser degree to normal cells. According to the invention, binding of the PMBC to the PNOM-cell should be a least 30% greater than its binding to the normal cell.

The term "selective targeting" refers in the invention to the selective binding of a compound to PNOM-cells, i.e., binding to the PNOM-cell in an extent being at least 30% greater than the binding to normal cells.

The term "diagnostic perturbed membrane-binding compound" (diagnostic PMBC) refers to a compound capable of selective targeting PNOM-cells, wherein the compound comprises or is linked to a marker, whereas the marker is detectable by means known to those skilled in the art.

The term "therapeutic perturbed membrane-binding compound" (therapeutic PMBC) refers to a PNC as defined above, comprising a drug, useful in the treatment of disease.

The term "solid support" refers in the contents of the present invention to a solid matrix, an insoluble matrix, or an insoluble support. The solid support in accordance with the present invention may be formed in a variety of structures such as a stack of micro-particulates, micro-filters, or micro-capillara.

The PMBC is used in an embodiment of the invention for the preparation of an agent for selective targeting PNOM-cells.

In one aspect, the present invention provides a compound which selectively targets a PNOM-cell (i.e., a PMBC) wherein the compound is represented by the structure set forth in formula (I):

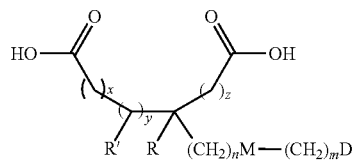

or pharmaceutically acceptable salts, metal chelates, solvates and hydrates of the compound represented by the structure as set forth in formula (I), and solvates and hydrates of the salts; wherein each of R and R' groups is independently selected at each occurrence from hydrogen, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched alkyl, linear or branched hydroxy-alkyl, linear or branched fluoro-alkyl, aryl or heteroaryl composed of one or two rings, or combinations thereof; n and m each stands for an integer of 0, 1, 2, 3 or 4; n and m may be same or different; M is selected from null, hydrogen, —O—, —S—, and —N(U), wherein U stands for hydrogen, or $C_1$, $C_2$, $C_3$, or $C_4$ alkyl; x, and z each stands independently and is an integer of 0, 1 or 2, where x and z can be the same or different; y is an integer of 0, 1 or 2, where when y=2 the substituent R' may be the same or different at each occurrence; and D is a marker for diagnostics, hydrogen, hydroxyl, or a drug; wherein the marker for diagnostics is selected from a marker for imaging such as F, wherein the F atom may be either $^{18}$F. or $^{19}$F, or a radio-labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). Alternatively, D is a drug to be targeted to the PNOM cells.

The drug may be a medicinally-useful agent for the prevention, amelioration, or treatment of a specific disease and may be, for example, without being limited: an inhibitor of apoptosis, (e.g., a caspase inhibitor, antioxidant, modulator of the Bcl-2 system); an activator of cell death (e.g. an anticancer drug); or a modulator of blood coagulation, which may be an anticoagulant, an antithrombotic, or a thrombolytic agent. In such case, the drug is preferably selected among an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; or an anti-inflammatory drug or an immuno-modulatory drug. In an embodiment of the invention, there is provided a method for improvement of anti-cancer therapy, by targeting anti-cancer drugs to tumors, via targeting the drug to foci of apoptosis, which occur within tumors either spontaneously, or in response to therapy. In another embodiment of the invention, there is provided a method of treating a thrombosis by targeting anticoagulants to the thrombus, so as to prevent, reduce or cease coagulation.

In another embodiment of the invention, D may be a solid support.

In another embodiment of the invention there is provided a compound which selectively targets a PNOM cell represented by the structure as set forth in formula (II):

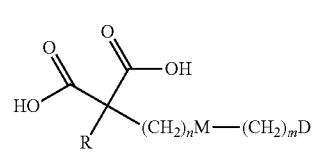

including pharmaceutically acceptable salts hydrates, solvates and metal chelates of the compound represented by the structure as set forth in formula (II) and solvates and hydrates of the salts; wherein R represents hydrogen or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched allyl, linear or branched hydroxy-allyl, linear or branched fluoro-alkyl, aryl or heteroaryl composed of one or two rings, or combinations thereof; n and m each stands for an integer of 0, 1, 2, 3 or 4; n and m may be same or different; M is selected from null, hydrogen, —O—, —S—, and —N(U), wherein U stands for a null, hydrogen, $C_1$, $C_2$, $C_3$, or $C_4$ alkyl; D is hydrogen or a marker for diagnostics. The marker for diagnostics may be in an embodiment of the invention a marker for imaging such as F, wherein the F may be $^{18}$F or $^{19}$F or a labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). Alternatively, D is a drug to be targeted to the PNOM-cells, as define above.

In another embodiment of the invention there is provided a compound represented by the structure as set forth in formula (III):

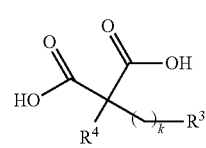

including pharmaceutically acceptable salts, hydrates, solvates and metal chelates of the compound represented by the structure as set forth in formula (III) and solvates and hydrates of the salts; wherein $R^3$ is hydroxyl or F; $R^4$ is $C_4$, $C_5$, $C_6$, $C_7$, $C_8$, $C_9$ or $C_{10}$ linear or branched alkyl, and k is an integer selected from 0, 1, 2, 3, 4 and 5.

In another embodiment of the invention there is provided a compound represented by the structure as set forth in formula (IV):

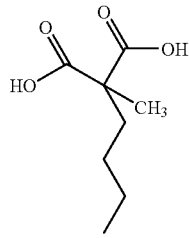

IV including pharmaceutically acceptable salts, hydrates, solvates and metal chelates of the compound represented by the structure as set forth in formula (IV) and solvates and hydrates of the salts; the compound is designated NST200.

In another embodiment of the invention there is provided a compound represented by the structure as set forth in formula (V):

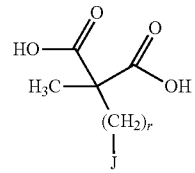

V including pharmaceutically acceptable salts hydrates, solvates and metal chelates of the compound represented by the structure as set forth in formula (V) and solvates and hydrates of the salts; wherein J is —F or —OH, and r stands for an integer of 4, 5, 6, 7, 8, 9, 10. In the case that r is 4 and J is —F, the compound is designated NST201. In the case that r is 5 and J is —F, the compound is designated NST-MiL-10.

In yet another embodiment of the invention there is provided a compound represented by the structure as set forth in formula (VI):

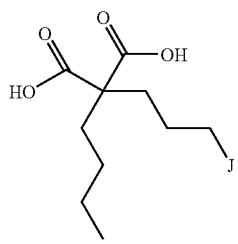

VI including pharmaceutically acceptable salts hydrates, solvates and metal chelates of the compound represented by the structure as set forth in formula (VI) and solvates and hydrates of the salts; wherein J is selected from hydrogen, —F and —OH. In the case that J is —F, the compound is designated NST205.

In another embodiment of the invention there is provided a compound represented by the structure set forth in formula VII:

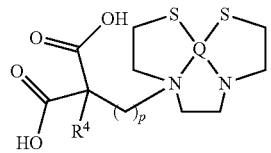

VII including pharmaceutically acceptable salts hydrates and solvates of the compound represented by the structure as set forth in formula (VII) and solvates and hydrates of the salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5.

In another embodiment of the invention there is provided a compound represented by the structure set forth in formula VIII:

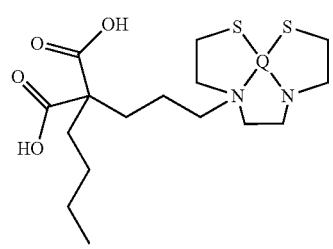

VIII including pharmaceutically acceptable salts, hydrates and solvates of the compound represented by the structure as set forth in formula (VIII) and solvates and hydrates of the salts, wherein Q is selected from technetium, oxo-technetium, rhenium and oxo-rhenium.

In another embodiment of the invention there is provided a compound represented by the structure as set forth in formula (IX):

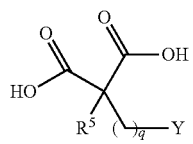

IX including pharmaceutically acceptable salts, hydrates, solvates and metal chelates of the compound represented by the structure as set forth in formula (IX) and solvates and hydrates of the salts; wherein $R^5$ is selected from hydrogen, $C_1$, $C_2$, $C_3$, $C_4$, $C_5$, and $C_6$ linear or branched alkyl, $C_1$, $C_2$, $C_3$, $C_4$, $C_5$, and $C_6$ linear or branched fluoro-allyl, and $C_1$, $C_2$, $C_3$, $C_4$, $C_5$, and $C_6$ linear or branched hydroxy-alkyl; q stands for an integer, selected from 1, 2, 3, 4 and 5; and Y is a marker for fluorescence. In an embodiment of the invention, Y is selected from a dansyl-amide group and fluorescein.

In another embodiment of the invention there is provided a compound represented by the structure as set forth in formula (O:

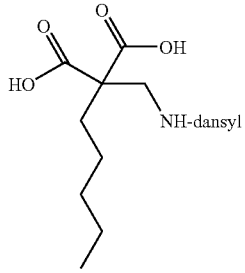

X including pharmaceutically acceptable salts hydrates, solvates and metal chelates of the compound represented by the structure as set forth in formula (X) and solvates and hydrates of the salts; The compound is designated NST203.

In another embodiment of the invention there is provided a compound represented by the structure as set forth in formula (XI):

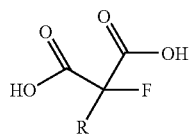

XI including pharmaceutically acceptable salts hydrates, solvates and metal chelates of the compound represented by the structure as set forth in formula (XI) and solvates and hydrates of the salts; wherein R represents hydrogen or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched allyl, linear or branched hydroxy-alkyl, linear or branched fluoro-alkyl, aryl or heteroaryl composed of one or two rings, or combinations thereof.

In another embodiment of the invention, there is provided a compound represented by the structure set forth in formula (XII):

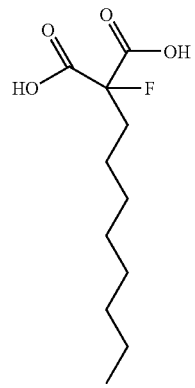

including pharmaceutically acceptable salts, hydrates, solvates and metal chelates of the compound represented by the structure as set forth in formula (XII) and solvates and hydrates of the salts; wherein F may be $^{18}F$ or $^{19}F$.

In another embodiment of the invention there is provided a compound represented by the structure as set forth in formula (XIII):

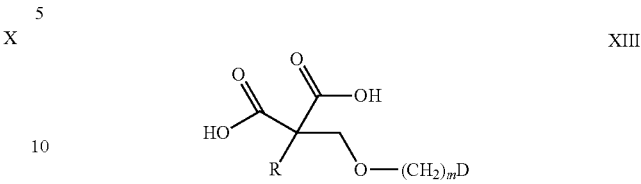

XIII including pharmaceutically acceptable salts, hydrates, solvates and metal chelates of the compound represented by the structure as set forth in formula (XIII) and solvates and hydrates of the salts; R represents hydrogen or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched alkyl, linear or branched hydroxy-allyl, linear or branched fluoro-alkyl, aryl or heteroaryl composed of one or two rings, or combinations thereof; m stands for an integer of 0, 1, 2, 3 or 4; D is a marker for diagnostics which may be in an embodiment of the invention a marker for imaging such as F, wherein the F may be $^{18}F$ or $^{19}F$ or a labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). Alternatively, D is a drug to be targeted to the PNOM-cells, as define above.

In another embodiment of the invention, there is provided a compound represented by the structure set forth in formula (XIV):

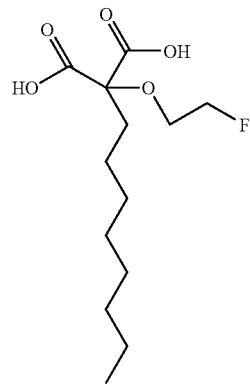

including pharmaceutically acceptable salts, hydrates, solvates and metal chelates of the compound represented by the structure as set forth in formula (XIV) and solvates and hydrates of the salts; wherein F may be $^{18}F$ or $^{19}F$.

In another aspect of the invention, there is provided a pharmaceutical composition for targeting of drugs to foci of apoptosis or blood clotting in a patient, wherein the patient may be a human or non-human mammal, wherein the pharmaceutical composition comprising a compound according to the structure set forth in formulae I, II, III, IV, V, VI, VII, VIII, IX, X, XI XII, XIII, or XIV wherein the compound comprises or is being linked to a drug.

In an aspect of the invention, there is provided a method of selectively targeting a medicinally-useful compound to PNOM-cells being within a population of cells, the method comprising: contacting the cell population with a compound represented by the structure set forth in any one of formulae I, II, m, IV, V, VI, VII, VIII, IX, X, XI, XII, XIII, or XIV, thereby selectively targeting the medicinally-useful compound to the PNOM-cells within the cell population.

In another aspect of the invention, there is provided a method of detecting a PNOM-cell within a cell population, the method comprising: (i). contacting the cell population with compound represented by the structure set forth in any one of formulae I, II, III, IV, V, VI, VII, VIII, IX, X, XI, XII, XIII, or XIV, or pharmaceutically acceptable salts, metal chelates, solvates and hydrates of the compound represented by the structure as set forth in any one formulae I, II, III, IV, V, VI, VII, VIII, IX, X, XI, XII, XIII, or MV, and solvates and hydrates of the salts; and (ii). determining the amount of the compound bound to the cells, wherein a significant amount of the compound bound to a cell indicates that the cell is being a PNOM-cell.

In another aspect of the invention, there is provided a method for detecting of PNOM-cells in a patient or an animal, the method comprising: (i), administering to the patient or animal a compound represented by the structure set forth in formulae I, II, III, IV, V, VI, VII, VIII, IX, X, XI, XII, XIII, or XIV, or pharmaceutically acceptable salts, metal chelates, solvates and hydrates of the compound represented by the structure as set forth in formulae I, II, III, IV, V, VI, VII, VIII, IX, X, XI, XII, XIII, or XIV, and solvates and hydrates of the salts; and (ii) imaging the examined patient or animal, so as determine the amount of the compound bound to cells, wherein a significant amount of compound bound to a cell indicates that the cell is a PNOM-cell.

In another aspect of the invention, there is provided a pharmaceutical composition for targeting of drugs to foci of apoptosis or foci or activated platelets in a blood clot in a patient or an animal, the pharmaceutical composition comprising a compound according to the structure set forth in formulae I, II, III, IV, V, VI, VII, VIII, IX, X, XI, XII, XIII, or XIV, wherein the compound comprises or is being linked to a drug.

In another embodiment, the invention provides a method of detecting cells undergoing a death process within a tumor in an examined subject, the method comprising: (i) administering to the examined subject a compound or a conjugate comprising the compound wherein said compound is represented by the structure set forth in formula (I):

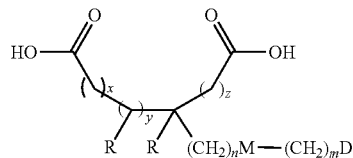

or pharmaceutically acceptable salts, metal chelates, solvates and hydrates of the compound represented by the structure as set forth in formula (I), and solvates and hydrates of the salts; wherein, one of R or R' groups is hydrogen, and the other of R or R' group represents $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched alkyl, linear or branched hydroxy-alkyl, linear or branched fluoro-alkyl, aryl or heteroaryl composed of one or two rings, or combinations thereof; n and m each stands for an integer of 0, 1, 2, 3 or 4; n and m may be same or different; M is selected from null, hydrogen, —O—, —S—, and —N(U), wherein U stands for hydrogen, or $C_1$, $C_2$, $C_3$, or $C_4$ alkyl; x, and z each stands independently and is an integer of 0, 1 or 2, where x and z can be the same or different; y is an integer of 0, 1 or 2, where when y=2 the substituent R' may be the same or different at each occurrence; and D is a marker for diagnostics. The marker for diagnostics may be in an embodiment of the invention a marker for imaging such as P, wherein the F may be $^{18}F$ or $^{19}F$ or a labeled metal chelate; the marker for imaging being selected from the group comprising a fluorescent label, a radio-label, a marker for X-ray, a marker for MRI, a marker for PET scan and a label capable of undergoing an enzymatic reaction that produces a detectable color; and (ii) determining the amount of the compound bound to the examined tumor of the patient, wherein detection of a significant amount of the compound bound to cells in the tumor indicates that these tumor cells are undergoing a death process.

In another embodiment, the invention provides a method of detecting cells undergoing a death process within a tumor in an examined subject, the method comprising: (i) administering to the examined subject a compound according to the structure set forth in formulae I, II, III, IV, V, VI, VII, VIII, IX, X, XI, XII, XIII, or XIV, wherein the compound comprises or is linked to a marker for imaging or a labeled metal chelate; and (ii) determining the amount of the compound bound to cells within the tumor, wherein detection of a significant amount of the compound bound to cells in the tumor indicates that these tumor cells are undergoing a death process.

In another embodiment, there is provided a method of targeting anticancer drugs to a tumor which has foci of apoptotic cells, the method comprising the step of administering a compound as set forth in any of the formulae I, II, III, IV, V, VI, VII, VIII, IX, X, XI, XII, XIII, or XIV, which either comprises a cytotoxic drug or is being linked to a cytotoxic drug, thereby achieving targeting of the drug to the foci of cell death within the tumor.

In another embodiment, there is provided a method of targeting an anticoagulant or a fibrinolytic agent to a blood clot, comprising the step of administering a compound as set forth in any of the formulae I, II, III, IV, V, VI, VII, VIII, IX, X, XI, XII, XI, or XIV, which either comprises the anticoagulant or fibrinolytic agent, thereby achieving targeting of the drugs to a blood clot.

BRIEF DESCRIPTION OF THE DRAWINGS

FIG. 5 A-C shows effect of chemotherapy on carcinoma cell death as detected by tritium-labeled NST200.

FIG. 7 demonstrates a table showing the ratio between the uptake in carcinoma tumor and other body organ before and after chemotherapy.

FIGS. 8 (A and B) demonstrates uptake of tritium-labeled NST200 into colon carcinoma and the effect of chemotherapy on the same (FIG. 8A).

FIGS. 10 (A and B) demonstrates autoradiography by tritium-labeled NST200 of rat renal ischemia reperfusion; (A) damaged kidney; (B) intact kidney.

FIGS. 11 (A and B) demonstrates autoradiography by tritium-labeled NST205 in a rat model of radiocontrast-induced acute distal tubular necrosis; (A) damaged kidney; (B) intact kidney.

DETAILED EMBODIMENTS OF THE INVENTION

Figure 1:
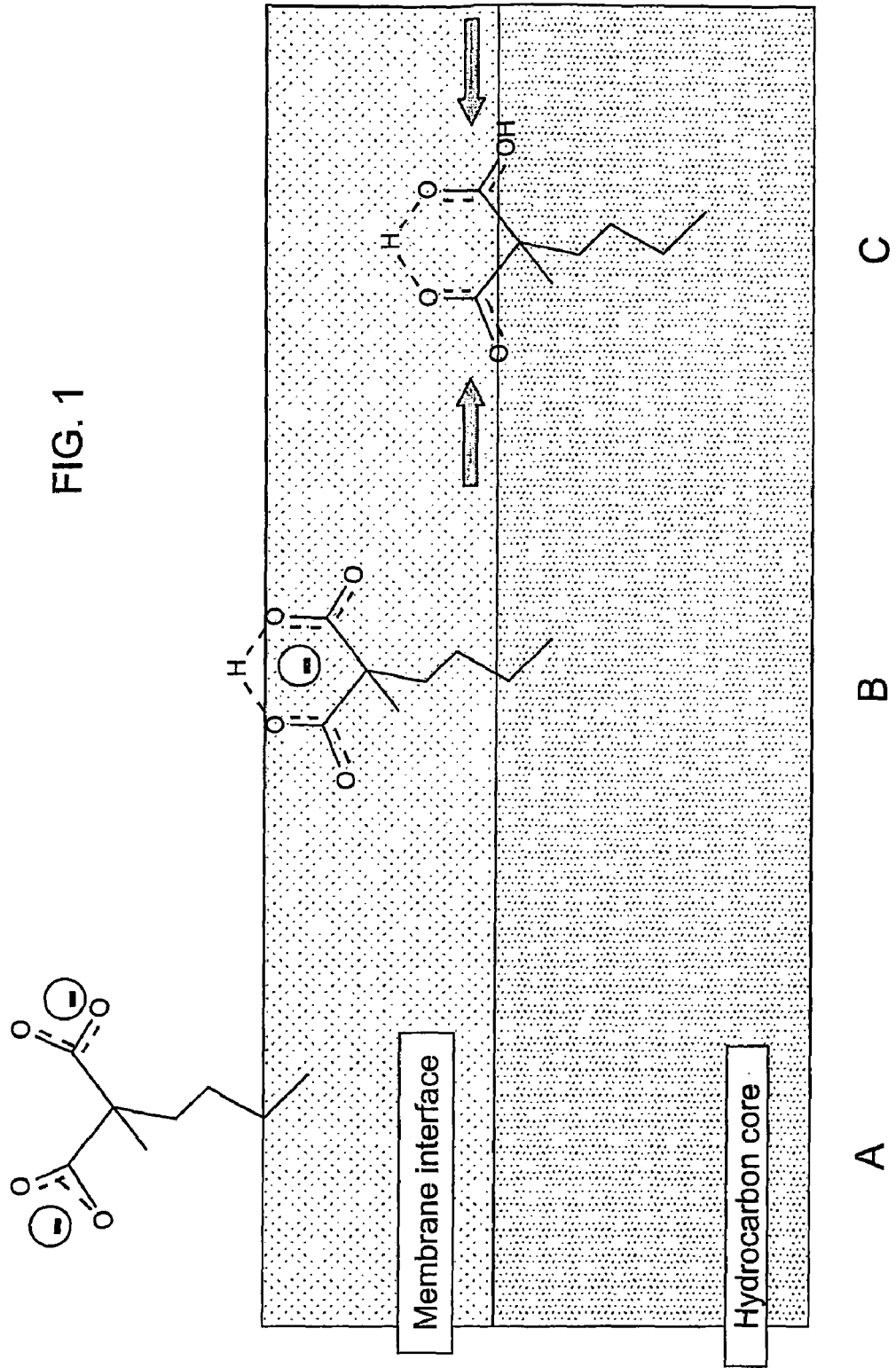
FIG. 1 demonstrates a scheme of the mechanism of action of the compounds of the invention: the NST-ML-Action Motif.

The present invention is related to compounds, capable of performing selective binding to cells undergoing perturbation of their normal organization of their plasma membrane (PNOM-cells), while binding to a lesser degree to cells maintaining the normal organization of their plasma membrane. The PNOM-cells are selected from cells undergoing a death process, apoptotic cells and activated platelets. The invention further relates to methods of detecting PNOM-cells by using compounds, which selectively bind to the PNOM-cells.

The compounds of the invention have the advantage of being active in performing selective targeting of PNOM-cells, while also featuring a relatively low molecular weight, and a potentially favorable pharmacokinetic profile. In one embodiment of the invention, there is provided a compound which selectively targets to a PNOM cell (i.e., a PMBC) wherein the compound is represented by the structure set forth in formula (I):

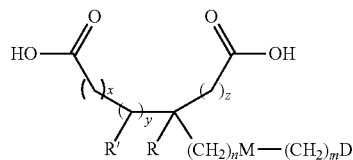

or pharmaceutically acceptable salts, metal chelates, solvates and hydrates of the compound represented by the structure as set forth in formula (–), and solvates and hydrates of the salts; wherein each of R and R' groups is independently selected at each occurrence from hydrogen, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched alkyl, linear or branched hydroxy-alkyl, linear or branched fluoro-alkyl, aryl or heteroaryl composed of one or two rings, or combinations thereof; n and m each stands for an integer of 0, 1, 2, 3 or 4; n and m may be same or different; M is selected from null, hydrogen, —O—, —S—, and —N(U), wherein U stands for hydrogen, or $C_1$, $C_2$, $C_3$, or $C_4$ alkyl; x, and z each stands independently and is an integer of 0, 1 or 2, where x and z can be the same or different; y is an integer of 0, 1 or 2, where when y=2 the substituent R' may be the same or different at each occurrence; and D is a marker for diagnostics, which in one embodiment of the invention may be a marker for imaging such as F, wherein the F may be $^{18}$F or $^{19}$F or a labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). In another embodiment, D is a drug to be targeted to the PNOM cells.

The drug may be a medicinally-useful agent for the prevention, amelioration, or treatment of a specific disease and may be, for example, without being limited: an inhibitor of apoptosis, (e.g., a caspase inhibitor, antioxidant, modulator of the Bcl-2 system); an activator of cell death (e.g. an anticancer drug); or a modulator of blood coagulation, which may be an anticoagulant, an antithrombotic, or a thrombolytic agent. In such case, the drug is preferably selected among an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; or an anti-inflammatory drug or an immuno-modulatory drug. In an embodiment of the invention, there is provided a method of targeting the drug to the area of interest, such as a focus of apoptosis in tumor, in order to achieve killing of the tumor cells. In another embodiment of the invention, there is provided a method of treating thrombosis by targeting an anticoagulant or a fibrinolytic agent to the thrombotic area, so as to prevent, reduce or cease coagulation.

In another embodiment of the invention, D may be a solid support.

In another embodiment of the invention, there is provided a compound which selectively targets PNOM cells, the compound being represented by the structure as set forth in formula (II):

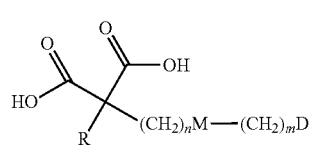

including pharmaceutically acceptable salts, hydrates, solvates and metal chelates of the compound represented by the structure as set forth in formula (II) and solvates and hydrates of the salts; wherein R represents hydrogen or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, linear or branched alkyl, linear or branched hydroxy-alkyl, linear or branched fluoro-alkyl, aryl or heteroaryl composed of one or two rings, or combinations thereof; n and m each stands for an integer of 0, 1, 2, 3 or 4; n and m may be same or different; M is selected from null, hydrogen, —O—, —S—, and —N(U), wherein U stands for a null, hydrogen, $C_1$, $C_2$, $C_3$, or $C_4$ alkyl; D is hydrogen or a marker for diagnostics, selected from a marker for imaging such $^{18}$F, or a labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). Alternatively, D is a drug to be targeted to the PNOM cells, as defined above.

In another embodiment of the invention there is provided a compound represented by the structure as set forth in formula (III):

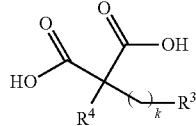

III including pharmaceutically acceptable salts, hydrates, solvates and metal chelates of the compound represented by the structure as set forth in formula (III) and solvates and hydrates of the salts; wherein $R^3$ is hydroxyl or F; $R^4$ is $C_4$, $C_5$, $C_6$, $C_7$, $C_8$, $C_9$ or $C_{10}$ linear or branched allyl, and k is an integer selected from 0, 1, 2, 3, 4 and 5.

In another embodiment of the invention there is provided a compound represented by the structure as set forth in formula (IV):

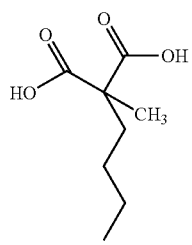

IV including pharmaceutically acceptable salts hydrates, solvates and metal chelates of the compound represented by the structure as set forth in formula (IM) and solvates and hydrates of the salts; the compound is designated NST200.

In another embodiment of the invention there is provided a compound represented by the structure as set forth in formula (V):

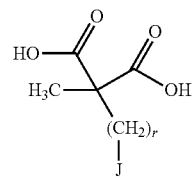

V including pharmaceutically acceptable salts hydrates, solvates and metal chelates of the compound represented by the structure as set forth in formula (V) and solvates and hydrates of the salts; wherein J is —F and —H, and r stands for an integer of 4, 5, 6, 7, 8, 9, 10. In the case that r is 4 and J is —F, the compound is designated NST201. In the case that r is 5 and J is —F, the compound is designated NST-ML-10.

In yet another embodiment of the invention there is provided a compound represented by the structure as set forth in formula (VI):

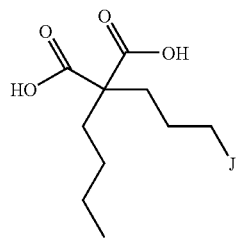

VI including pharmaceutically acceptable salts hydrates, solvates and metal chelates of the compound represented by the structure as set forth in formula (VI) and solvates and hydrates of the salts; wherein J is selected from hydrogen, —F and —OH. In the case that J is —F, the compound is designated NST205.

In another embodiment of the invention there is provided a compound represented by the structure set forth in formula VII:

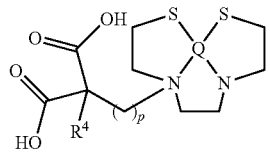

VII including pharmaceutically acceptable salts, hydrates and solvates of the compound represented by the structure as set forth in formula (VII) and solvates and hydrates of the salts, wherein Q is selected from Technetium, oxo-Technetium, Rhenium and oxo-Rhenium, $R^4$ is selected from hydrogen, $C_1$, $C_2$, $C_3$, $C_4$, $C_5$, and $C_6$ linear or branched alkyl, and p stands for an integer, selected from 1, 2, 3, 4 and 5.

In another embodiment of the invention there is provided a compound represented by the structure set forth in formula VIII:

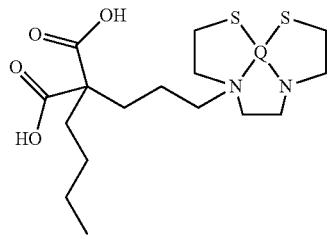

VIII including pharmaceutically acceptable salts, hydrates and solvates of the compound represented by the structure as set forth in formula (VIII) and solvates and hydrates of the salts, wherein Q is selected from technetium, oxo-technetium, rhenium and oxo-rhenium.

In another embodiment of the invention there is provided a compound represented by the structure as set forth in formula (IX):

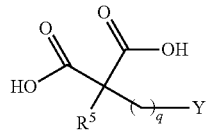

including pharmaceutically acceptable salts, hydrates, solvates and metal chelates of the compound represented by the structure as set forth in formula (IX) and solvates and hydrates of the salts; wherein $R^5$ is selected from hydrogen, $C_1, C_2, C_3, C_4, C_5$, and $C_6$ linear or branched allyl, $C_1, C_2, C_3, C_4, C_5$, and $C_6$ linear or branched fluoro-alkyl, and $C_1, C_2, C_3, C_4, C_5$, and $C_6$ linear or branched hydroxy-alkyl; q stands for an integer, selected from 1, 2, 3, 4 and 5; and Y is a marker for fluorescence. In an embodiment of the invention, Y is selected from a dansyl-amide group and fluorescein.

In another embodiment of the invention there is provided a compound represented by the structure as set forth in formula (X):

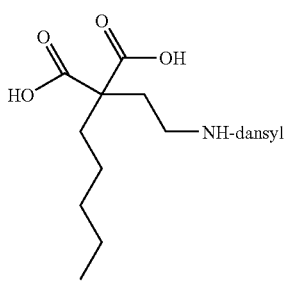

including pharmaceutically acceptable salts, hydrates, solvates and metal chelates of the compound represented by the structure as set forth in formula (X) and solvates and hydrates of the salts; The compound is designated NST203.

In another embodiment of the invention there is provided a compound represented by the structure as set forth in formula (XI):

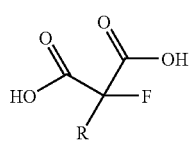

including pharmaceutically acceptable salts, hydrates, solvates and metal chelates of the compound represented by the structure as set forth in formula (X) and solvates and hydrates of the salts; wherein R represents hydrogen or $C_1, C_2, C_3, C_4, C_5, C_6, C_7, C_8, C_9, C_{10}, C_{11}, C_{12}, C_{13}, C_{14}, C_{15}, C_{16}$, linear or branched allyl, linear or branched hydroxy-alkyl, linear or branched fluoro-alkyl, aryl or heteroaryl composed of one or two rings, or combinations thereof.

In another embodiment of the invention, there is provided a compound represented by the structure set forth in formula (XII):

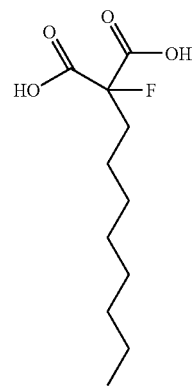

including pharmaceutically acceptable salts hydrates, solvates and metal chelates of the compound represented by the structure as set forth in formula (XII) and solvates and hydrates of the salts; wherein F may be $^{18}F$ or $^{19}F$.

In another embodiment of the invention there is provided a compound represented by the structure as set forth in formula (XIII):

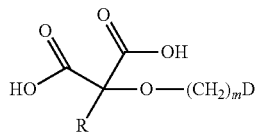

including pharmaceutically acceptable salts hydrates, solvates and metal chelates of the compound represented by the structure as set forth in formula (XIII) and solvates and hydrates of the salts; R represents hydrogen or $C_1, C_2, C_3, C_4, C_5, C_6, C_7, C_8, C_9, C_{10}, C_{11}, C_{12}, C_{13}, C_{14}, C_{15}, C_{16}$, linear or branched alkyl, linear or branched hydroxy-allyl, linear or branched fluoro-alkyl, aryl or heteroaryl composed of one or two rings, or combinations thereof; m stands for an integer of 0, 1, 2, 3 or 4; D is hydrogen or a marker for diagnostics, which may be in an embodiment of the invention a marker for imaging such as F, wherein the F may be $^{18}F$ or $^{19}F$ or a labeled metal chelate; the marker for imaging may be detected by color, fluorescence, x-ray, CT scan, magnetic resonance imaging (MRI) or radio-isotope scan such as single photon emission tomography (SPECT) or positron emission tomography (PET). Alternatively, D is a drug to be targeted to the PNOM-cells, as define above.

In another embodiment of the invention, there is provided a compound represented by the structure set forth in formula (XIV):

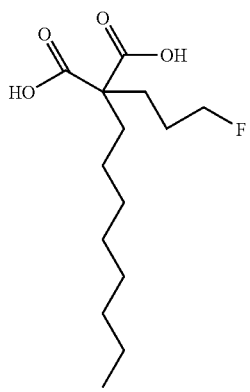

including pharmaceutically acceptable salts hydrates, solvates and metal chelates of the compound represented by the structure as set forth in formula (XIV) and solvates and hydrates of the salts; wherein F may be $^{18}$F or $^{19}$F.

In another embodiment of the invention each of the compounds represented by formulae I, II, III, IV, V, VI, VII, VIII, IX, X, XI, XII, XIII, or XIV, may comprise or may be linked to a marker for diagnostics such as for example without being limited Tc, Tc=O, In, Cu, Ga, Xe, Tl, Re and Re=O, $^{123}$I, $^{131}$I, Gd(III), Fe(III), Fe$_2$O$_3$, Fe$_3$O$_4$, Mn(II) $^{18}$F, $^{15}$O, $^{18}$O, $^{11}$C, $^{13}$C, $^{124}$I, $^{13}$N, $^{75}$Br, Tc-99m or In-111.

In another aspect of the invention, there is provided a method of detecting a PNOM-cell within a cell population, the method comprising: (i). contacting the cell population with a compound represented by any one of the structure set forth in formulae I, II, III, IV, VI, VII, VI, IX, X, XI, XII, XIII, or XIV, or pharmaceutically acceptable salts, metal chelates, solvates and hydrates of the compound represented by the structure as set forth in formulae I, II, IV, IV V, VI, VII, VIII, IX, X, XI, XII, XII, or XIV, and solvates and hydrates of the salts; and (ii). determining the amount of the compound bound to the cells, wherein a significant amount of compound bound to a cell indicates its being a PNOM-cell.

The term "significant amount of the compound bound to a cell" refers according to the invention to the amount of the compound of the invention, comprising or is being attached to a marker for diagnostics, which binds to a PNOM-cell in an amount which is at least 30% greater than the amount bound to a normal cell. In another embodiment, the amount may be higher by 50%. In another embodiment of the invention, the amount may be higher by 75%. In another embodiment, the amount may be higher by 150%. In another embodiment the amount may be higher by about two fold. In another embodiment the amount may be higher than at least two fold. In another embodiment, the amount may be higher than at least five fold. In another embodiment, the amount may be higher by at least ten fold.

In an embodiment of the invention, relating to use of the compounds of the invention for obtaining images of cells undergoing a death process in a patient via radionuclide imaging by PET or SPECT, the calculation of the ratio between the amount of the compound bound to the PNOM-cells vs. the amount bound to normal cells may be conducted by comparing the amplitude or intensity of the signal obtained from the tissue inflicted by the death process, with the amplitude/intensity obtained from an organ not-inflicted by the process.

According to another aspect of the invention, there is provided a method for detecting of PNOM-cells in a patient or an animal, the method comprising: (i) administering to the patient or animal a compound represented by the structure set forth in formulae I, II, III, IV, V, VI, VII, VIII, IX, X, XI, XII, XIII, or XIV, wherein the compound comprises a marker for imaging, such as $^{18}$F or pharmaceutically acceptable salts, metal chelates, solvates and hydrates of the compound represented by the structure as set forth in formulae I, II, III, IV, V, VI, VII, VIII, IX, X, XI, XII, XIII, or XIV, and solvates and hydrates of the salts; and (ii) imaging the examined patient or animal, so as to determine the amount of compound bound to cells, wherein detection of a significant amount of compound bound to cells indicates that these cells are PNOM-cells.

The mechanism of action of the compounds of the invention comprises, at least in part, the activity of a module shared by all the compounds, having the general formula XV, and designated NST-ML-Action Motif:

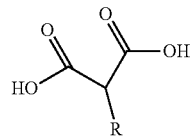

wherein R stands for an alkyl. In an embodiment of the invention, R is butyl.

The NST-ML-Action Motif is designed to correspond to the structural alterations encountered in the plasma membranes of apoptotic cells, which distinguish these membranes from the membranes of healthy cells. This complex of membrane alterations comprises:

(i). Scrambling of membrane phospholipids, with exposure on the cell surface of phosphatidylethanolamine (PE) and the negatively-charged phosphatidylserine (PS). Exposure of PS on the cell surface leads to a negative surface electric potential, and attraction of protons form the bulk to the membrane interface.

(ii). The increase in the fraction of aminophospholipids (PE and PS) within the outer leaflet of the membrane results in an enhancement of the proton currents in the interface of the outer leaflet of the membrane (interfacial proton currents, IPC). This enhancement is due to the substantial increase in the number of functionalities amenable to participation in proton transfer reactions, as PE and PS replace phosphatidylcholine (PC) and sphingomeylin (SM) in the outer membrane leaflet. PE comprises a primary amine, while PS comprises a primary amine and a carboxyl group. By contrast, PC and SM comprise each a quaternaly ammonium, that bears a permanent positive charge, and thus cannot participate in proton transfer reactions.

(iii). In addition, apoptotic membranes are characterized by reduced level of packing of the membrane constituents and increased membrane fluidity.

In a non limiting hypothesis of the mode of action of the NST-ML-Action Motif, it comprises a switch moiety, activated selectively upon its approaching a membrane which features the above characteristics, i.e., the plasma membrane of an apoptotic cell (FIG. 1). The Action Motif is soluble in physiological pH, due to its having two negatively-charged carboxylate groups (pKa of alkylmalonate is about 5.6 and 2.8), thus having mostly a formal charge of −2 in physiological conditions. However, upon approaching the apoptotic membrane, due to the more acidic surface, and due to the reduction in the dielectric constant of the interfacial environment, which acts to elevate pKa values of the carboxyl groups, a proton is being captured by the malonate moiety.

The capture of the proton by the malonate group neutralizes one of the negative charges, thus rendering the molecule more hydrophobic, with an overall charge of −1. Moreover, the capture of the proton further leads to a very unique situation, which includes the following:

(i). An acid-anion pair is formed, wherein an exceptionally strong hydrogen bond is formed between the protonated and unprotonated carboxyl groups. This hydrogen bond is strong, symmetrical and stabilized by resonance and tautomerization.

(ii). This leads to distribution of the negative charge over the four carboxyl atoms, i.e., its being partially delocalized.

(iii). The strong acid-anion hydrogen bond rigidifies the molecule, creating a bulky, rigid, flat, six-memebered ring, bearing a partially-delocalized negative charge, and comprising pi-electron clouds over the carboxyl double bonds. Such an element can undergo a relatively favorable penetration into the membrane interface, according to a non-limiting hypothesis of the mechanism of action of the compounds of the invention. However, its bulky, rigid structure directs its binding selectively to loosely packed emebranes, i.e., apoptotic membranes, while precluding binding to highly-packed membranes, such as the plasma membranes of healthy cells. These steric features therefore promote selectivity in binding to the apoptotic membranes.

Upon the selective penetration of the single-protonated malonate into the membrane interface of the apoptotic cell, it becomes subjected to the enhanced interfacial proton currents, and becomes integrated within the enhanced interfacial network of hydrogen bonds. The probability for a second proton to be acquired by the malonate moiety under these conditions is markedly increased. This will further lead to neutralization of charge and formation of further acid-anion pairs with adjacent phospholipid molecules. Taken together, these events will act to stabilize the binding of the molecule to the interface of the apoptotic membrane.

The penetration of the protonated malonate moiety into the membrane interface and the stabilization of its binding in the interface, allow the alkyl chain R to traverse the membrane interface and to reach its optimal binding environment, i.e., the membrane hydrocarbon core, whereupon it will further contribute through hydrophobic interactions to the free energy gain of compound binding.

The NST-ML-Action Motif is being utilized for useful diagnostic or therapeutic purposes, through its binding to a marker for imaging or a therapeutic drug (moiety D in Formula I) through a hydrocarbon linker [$(CH_2)_m$ of Formulae I or 2]. The NST-ML-Action Motif according to this approach acts as a targeting moiety, allowing selective targeting of the marker for imaging or the drug attached to it to cells and tissues inflicted by cell death, particularly apoptosis, or tissues inflicted by platelet activation and thrombosis.

FIG. 1 demonstrates NST200 (Formula IV), and describes the three stages of its approach and binding to the PNOM membrane in physiological conditions:

A: The compound is in an aqueous solution, thus both carboxyl groups are deprotonated, i.e., negatively charged, and the compound is highly soluble.

B: Upon approaching the negatively-charged apoptotic membrane, the compound acquires a proton. An anion-acid dimer is formed, thus creating a stable six-membered, resonance-stabilized ring, which penetrates the membrane interface. The bulky, rigid ring structure assists in selectivity, since its steric features favor binding to the more loosely-packed plasma membrane of the apoptotic cell, rather than binding to the well-packed plasma membrane of the healthy cell.

C: Upon penetration of the compound into the membrane interface, it is subjected to the interfacial network of hydrogen bonds, and to the augmented interfacial proton currents encountered in the interface of the apoptotic membrane. The resultant protonation and hydrogen bonding further acts to stabilize the binding of the compound to the interface (arrows). Such penetration further allows the alkyl chain to reach its optimal position within the membrane, thus further contributing to the binding energy, through formation of hydrophobic interactions with the membrane hydrocarbon core.

The compounds of the invention may be used for selective targeting of medicinally-useful agents to tissues and organs comprising PNOM-cells, in three different approaches of the invention:

(i). According to a first approach, termed hereinafter the "detection approach", the selective binding may be utilized to targeting a marker for imaging to PNOM-cells. This may be used in clinical practice, either in vivo, ex vivo or in vitro, for the diagnosis of diseases in which such cells emerge as will be explained herein below.

(ii). According to a second approach, termed hereinafter the "therapeutic approach", the properly of selective binding is used for selective targeting of therapeutic agents to organs and tissues in the body wherein PNOM-cells emerge, e.g., regions of cell death, thrombus formation or inflammation.

(iii). In accordance with a third approach of the invention termed the "clearance approach", the selective binding of the compounds of the invention to PNOM-cells is utilized, via attachment of the compounds to a solid support, to clear body fluids such as blood from PNOM-cells, which may be potentially hazardous due to their pro-coagulant properties.

In accordance with the detection approach, the present invention concerns a composition comprising a PMBC as an effective ingredient, comprising or linked to a marker for imaging, for the detection of PNOM-cells, either in vitro, ex vivo or in vivo. Such a PMBC is hereinafter designated "diagnostic PMBC". The diagnostic PMBC is capable of performing selective binding to PNOM-cells present in the assayed sample. Then, the binding may be identified by any means known in the art. The diagnostic PMBC of the invention enables the targeting of the marker, by the PMBC, to PNOM cells in a selective manner. Then, the detectable label can be detected by any manner known in the art, and in accordance with the specific label used, for example, fluorescence, radioactive emission, or a color production, MRI, x-ray and the like. In one embodiment, the diagnostic PMBC is linked to the detectable label by a covalent or a non-covalent (e.g., electrostatic) binding.

In an embodiment, the detectable label may be any of the respective radio-isotopes of the metal ions Tc, oxo-Tc, In, Cu, Ga, Xe, Ti and Re, oxo-Re and the covalently linked atoms: $^{123}$I and $^{131}$I for radio-isotope scan such as SPECT; Gd(III), Fe(III) or Mn(II) for MRI; and $^{18}$F, $^{15}$O, $^{18}$O, $^{11}$C, $^{13}$C, $^{124}$I, $^{13}$N and $^{75}$Br for positron emission tomography (PET) scan.

In an embodiment, the PMBC of the invention is aimed at clinical imaging of apoptosis via PET scan, and the PMBC comprises $^{18}$F atom(s).

Due to the short half-life of certain radio-isotopes used as markers for imaging, such as $^{18}$F, the attachment of such marker for the purposes of clinical PET imaging may be performed immediately before the administration of the diagnostic compound to the patient. Therefore, it may be useful to synthesize a PMBC-PET precursor, comprising a moiety to be substituted by the radio-isotope such as $^{18}F$ before administration to the patient. In one embodiment, the moiety to be replaced by $^{18}F$ is selected from a hydroxyl group, a nitro group, or a halogen atom such as bromine or chlorine. Such a PMBC-precursor PMBC-PET precursor is also included in the scope of the invention.

The method for labeling a PMBC, which can be any PMBC of the structures described above, with $^{18}F$ for PET imaging, comprises the step of attaching an $^{18}F$ atom to the PMBC; thereby radio-labeling the PMBC with $^{18}F$ for PET imaging. Optionally, the functional groups of the PMBC may be protected by appropriate protecting groups prior to the step of attaching $^{18}F$ atom. Said protecting groups are thereafter optionally removed after the step of attachment of the $^{18}F$ atom.

In the case that the marker is a metal atom (e.g., Gd, $^{99m}Tc$ or oxo-$^{99m}Tc$ for MRI or SPECT, respectively), the PMBC comprises a metal chelator. The metal coordinating atoms of the chelator may be nitrogen, sulfur or oxygen atoms. In an embodiment of the invention, the chelator is diaminedithiol, monoamine-monoamide-bisthiol (MAMA), triamide-monothiol, and monoamine-diamide-monothiol. In such case, both a PMBC-chelate precursor, being the PMBC attached to or comprising a chelator prior to complexation with the metal atom, and the complex comprising the metal atom, are included in the scope of the invention.

For fluorescent detection, the diagnostic PMBC may comprise a fluorescent group selected from any fluorescent probe known in the art. Examples for such probes are 5-(dimethylamino) naphthalene-1-sulfonylamide (dansyl-amide), and fluorescein.

The compounds of the invention may be used for the detection and diagnosis of a wide variety of medical conditions, characterized by formation PNOM-cells. Examples of clinical conditions characterized by PNOM-cells are as follows:

Diseases which are characterized by occurrence of excessive apoptosis, such as degenerative disorders, neurodegenerative disorders (e.g., Parkinson's disease, Alzheimer's disease, Huntington chorea), AIDS, ALS, Prion Diseases, myelodysplastic syndromes, ischemic or toxic insults, graft cell loss during transplant rejection; tumors, and especially highly malignant I aggressive tumors, are also often characterized by enhanced apoptosis in addition to the excessive tissue proliferation.

Example 3 of the invention as well as FIG. 2, exemplify the performance of a compound of the invention in detecting brain cells undergoing a death process. The trigger for the cell death was ischemia/reperfusion. The damaged brain hemisphere manifested markedly higher levels of uptake of tritium-labeled NST200, compared to the contralateral non-damaged hemisphere.

Diseases manifested by excessive blood clotting, wherein PNOM occurs during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by PNOM-cells, such as apoptotic macrophages, apoptotic smooth muscle cells, apoptotic endothelial cells, and activated platelets. Such activated platelets are encountered in the thrombi, often associated with the unstable atherosclerotic plaque.

The detection may also be carried out in a person already known to have the respective disease, for the purpose of evaluating disease severity and in order to monitor disease course and/or response to various therapeutic modalities. A non-limited example for such monitoring is evaluation of response to anticancer therapy. Since most anti-tumor treatments, such as chemotherapy or radiotherapy exert their effect by induction of apoptosis, detection by a diagnostic PMBC of therapy-induced apoptosis of tumor cells may teach on the extent of sensitivity of the tumor to the anti-tumor agent. This may substantially shorten the lag period between the time of administration of the anti-cancer treatment and the time of proper assessment of its efficacy.

Moreover, the detection may be also used to monitor adverse effects of anti-cancer treatments. A large part of such adverse effects is due to untoward treatment-induced apoptosis in normal, yet sensitive cells, such as those of the gastrointestinal epithelium or the bone marrow hematopoietic system.

In addition, the detection may aim at characterization of intrinsic apoptotic load within a tumor, often correlated with the level of tumor aggressiveness; and may also assist in the detection of metastases, via detection of the intrinsic apoptosis frequently occurring within metastases.

Similarly, the diagnostic PMBC of the invention may be useful in monitoring graft survival after organ transplantation, since apoptosis plays a major role in cell loss during graft rejection.

In addition, the detection may aim at monitoring response to cyto-protective treatments, and thus aid in screening and development of drugs which are capable of inhibiting cell loss in various diseases (for example those recited above) by enabling a measure of assessment of cell death.

The detection may also be useful for the detection of atherosclerotic plaques, since destabilization of such plaques, rendering them vulnerable, prone to rupture, thrombosis and embolization, is characterized by participation of several types of PNOM-cells, including apoptotic cells (apoptotic macrophages, smooth muscle cells and endothelial cells), and activated platelets.

In accordance with this approach, the present invention is related to a method of detection of PNOM-cells in a cell population, selected from whole body, organ, tissue, tissue culture or any other cell population, the method comprising: (i). contacting the cell population with a diagnostic PMBC according to any of the embodiments of the invention; and (ii). determining the amount of PMBC bound to the cell population, wherein detection of a significant amount of compound bound to a cell within the population indicates that the cell is a PNOM-cell.

The examples section show the ability of the ability of tritium-labeled NST 200, NST 203 and NST 205 to bind to apoptotic cells in higher amount than to control, non-apoptotic cells, demonstrate that the property of the compounds of the invention, in performing selective binding and detection of apoptotic cells.

In another embodiment, the present invention further relates to a method for detecting PNOM-cells in a patient or in an animal in vivo, the method comprising: (i). administering a diagnostic PMBC to the examined patient or animal; the administration being performed by any means known in the art, such as parenteral (e.g., intravenous) or oral administration; and (ii). imaging the examined patient or animal, by any method known in of the art (e.g., PET scan, SPECT, MRI), to detect and determine the amount of diagnostic-PMBC bound to cells, wherein a significant amount of compound bound to a cell indicates that the cell is a PNOM-cell.

In another embodiment of the invention, the present invention is related to a method for the detection of PNOM-cells in a tissue or cell culture sample in vitro or ex-vivo, the method comprising: (i). contacting the sample with a diagnostic PMBC, which may be any of the PMBC compounds described in the invention, under conditions enabling binding of the diagnostic PMBC to the biological membranes of PNOM-cells; and (ii). detecting the amount of diagnostic PMBC bound to the cells; the presence of a significant amount of bound diagnostic compound indicating the presence of PNOM-cells within the tissue or cell culture.

The step of detection in the in vivo or ex-vivo studies may be, for example, in the case of fluorescent-labeled compound of the invention, without limitation by using flow cytometric analysis, which permits cell visualization on equipment that is widely commercially available. In an example using fluorescence to visualize cells, a single 15 mW argon ion laser beam (488 nm) is used to excite the FITC fluorescence, and fluorescence data is collected using 530 nm band pass filter to provide a histogram. The percent of fluorescent cells can be calculated, for example using Lysis II software or any other software. The method for detection may be used in an embodiment of the invention for screening therapeutic drugs such as anticancer drugs.

The term "significant amount" according to the invention, means that the amount of PMBC bound to a PNOM-cell is at least 30% higher than the amount bound to a non-PNOM-cell. The actual amount may vary according to the imaging method and equipment utilized, and according to the organs or tissues examined. In another embodiment the amount of PMBC bound to a PNOM-cell is at least 50% higher than the amount bound to a non-PNOM-cell. In another embodiment the amount of PMBC bound to a PNOM-cell is at least 75% higher than the amount bound to a non-PNOM-cell. In another embodiment the amount of PMBC bound to a PNOM-cell is at least twice times the amount bound to a non-PNOM-cell. In another embodiment the amount of PMBC bound to a PNOM-cell is at least four times the amount bound to a non-PNOM-cell. In another embodiment the amount of PMBC bound to a PNOM-cell is at least six times the amount bound to a non-PM-cell. In another embodiment the amount of PMBC bound to a PNOM-cell is at least eight times the amount bound to a non-PNOM-cell. In another embodiment the amount of PMBC bound to a PNOM-cell is at least ten times the amount bound to a non-PNOM-cell.

The action of the binding depends inter-alia on the method of measuring the difference in binding. The method of the present invention may be used for the diagnosis of a disease characterized by the occurrence of PNOM-cells, for example, without being limited to any of the diseases mentioned above.

The method of the present invention may also be used for monitoring the effects of various therapeutic modalities used for treatment of diseases or medical conditions, or alternatively for basic science research purposes as explained above.

In accordance with a second approach of the invention, termed "the therapeutic approach", the present invention concerns a pharmaceutical composition comprising a PMBC, used for targeting an active drug or a pro-drug to PNOM-cells. A therapeutic PMBC according to the invention means a PMBC comprising a drug or a PMBC being conjugated to a medicinally-useful agent. The term "conjugate" means two molecules being linked together by any means known in the art.

The association between the medicinally-useful drug and the PMBC wherein it is comprised or linked to in the therapeutic PMBC may be by covalent binding, by non-covalent binding (e.g., electrostatic forces) or by formation of carrier particles (such as liposomes) comprising the drug and having on their surface a PMBC which targets the complex to the PNOM-cells. Once the drug reaches the target, it should be able to exert its physiological activity, either when still being part of the PMBC-conjugate, after disconnecting from the PMBC unit (for example by cleavage, destruction, etc., activity of natural enzymes), by phagocytosis of drug-containing liposomes having PMBC on their membrane, or by any other known mechanism.

The drug should be chosen in accordance with the specific disease for which the composition is intended.

The pharmaceutical composition, as well as the diagnostic composition of the invention may be administered by any of the known routes, inter alia, oral, intravenous, intraperitoneal, intramuscular, subcutaneous, sublingual, intraocular, intranasal or topical administration, or intracerebral administration. The carrier should be selected in accordance with the desired mode of administration, and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

In accordance with this aspect, the present invention still flirter concerns a method for treating a disease manifesting PNOM-cells, comprising administering to an individual in need of such treatment an effective amount of a therapeutic PMBC, the therapeutic PMBC comprising a drug being active as a treatment for the disease or a pro-drug to be converted to an active drug in the targeted area. The therapeutic PMBC allows for selective targeting of the drug to the tissues comprising PNOM-cells, thus augmenting its local concentration, and potentially enhancing its therapeutic effect at the target site. Such medical disorders are those defined above.

In another embodiment, there is provided a method of killing cancer cells in a tumor, comprising the step of targeting apoptotic cells within the tumor by administration of a therapeutic PMBC, comprising any one of the compounds set forth in formulae I, II, III, IV, V, VI, VII, VIII, IX, X, XI, XII, XIII, or XIV, and a cytotoxic drug, thereby killing the cancer cells. In one embodiment, the method of killing the tumor cells involves an "autocatalytic mechanism", whereby the amount of cytotoxic agent being targeted to the tumor increases with sequential doses, as each dose, due to its cytotoxic effect, enhances the load of apoptotic cells within the tumor, thus creating more sites for the targeting of the next dose of the therapeutic PMBC. Such strategy may enhance the efficacy of the anticancer treatment, and augment the chances for tumor eradication.

The term "effective amount" of the therapeutic PMBC refers to an amount capable of decreasing, to a measurable level, at least one adverse manifestation of the disease, and should be chosen in accordance with the drug used, the mode of administration, the age and weight of the patient, the severity of the disease, etc.

In another embodiment, the therapeutic PMBC of the invention comprises or is being linked to a radioisotope which has therapeutic effect. An Example without limitation for such a radio-isotope is Yittrium 90, Iodine 131, Rhenium 188, Holmium 166, Indium 111, Leutitium 177, or any other radioisotopes emitting radiation, which is useful for therapeutic purposes.

In another embodiment, there is provided a method for reducing/preventing a blood clot, by administration of a therapeutic PMBC, comprising any one of the compounds set forth in formulae I, II, III, IV, V, VI, VII, VIII, IX, X, XI, XII, XIII, or XIV, being linked to an anticoagulant or a fibrinolytic agent, thereby targeting the therapeutic agent to the activated platelets in the blood clot and reducing/preventing the thrombus formation.

This method may be used also to treat or prevent diseases manifested by excessive blood clotting, wherein PNOM occurs during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

According to a third approach of the invention, termed the "clearance approach", the properties of the PMBCs of the invention to bind specifically to PNOM-cells are utilized to clear body fluid of the cells. In an embodiment of the invention, the body fluid is blood or a blood product.

Many surgical or medical interventions requiring extracorporeal circulation are associated with exposure of blood elements to exogenous artificial environment. This often leads to activation of and damage to blood cells, systemic inflammation, and thromboembolic phenomena, potentially having serious clinical consequences, such as neurological dysfunction upon lodging of microemboli in the cerebral blood vessels. It is therefore desirable to detect and remove the damaged, activated or apoptotic cells from blood.

Thus, according to one of its aspects, the present invention concerns a PMBC immobilized on a solid support. The immobilization may be by direct attachment, either by covalent or non-covalent binding, or by attachment through a spacer. The immobilized PMBC is intended to clear a body fluid from PNOM-cells.

According to another embodiment of the present invention, the solid support features a plurality of beads to which the PMBC are bound. Preferably, the beads are resin-coated beads. Alternatively, the beads may be magnetic beads.

Where the solid support includes a plurality of fibers or micro-capillara, among and/or through which the body fluid flows, the inner and/or outer faces thereof are covered with the PMBC.

The compounds immobilized on a solid support form part of a filter device. Thus, in accordance with the clearance approach, the present invention further concerns a filter device comprising a housing containing the PMBC immobilized on the solid support, and a fluid inlet and fluid outlet. Body fluids such as blood or blood products enter the housing through the inlet, come into contact and adhere to the immobilized PMBC contained in the housing. Thus, the body fluid is cleared of circulating cells having perturbed membranes, such as damaged or dying cells, or cleared of larger structures such as emboli having PNOM membranes. Consequently, fluid exiting from the outlet has a reduced content of the PNOM-cells or is essentially devoid of same.

The filter device may form a replaceable, a permanent, or an add-on portion of an extracorporeal circulation apparatus. Thus the present invention also concerns an extracorporeal circulation apparatus comprising the filter device, wherein blood circulating through the apparatus also passes through the device.

Examples of such apparatuses are a cardiopulmonary bypass apparatus; a hemodialysis apparatus; a plasmapheresis apparatus and a blood transfusion apparatus, such as state of the art blood transfusion bags.

EXAMPLES

In order to understand the invention and to see how it may be carried-out in practice, the following examples are described: examples directed to synthesis of the compounds of the invention; and examples directed to the performance of the compounds of the invention in selective binding to cells undergoing death process. In order to allow detection of the compounds of the invention, they were radio-labeled with tritium and detected by measuring uptake to the damaged areas or by autoradiographic methods. In some of the Examples, the compounds were labeled by attachment to a fluorescent label, i.e., a dansylamide group, and detected by fluorescent microscopy. The selectivity of binding of the compounds to the apoptotic cells was demonstrated in vitro, in tissue cultures, and in vivo, in a murine model of cerebral stroke, wherein cell death was induced by occlusion of the middle cerebral artery, in murine models of kidney ischemic and toxic insults, in a murine model of melanoma, in a murine model of colon carcinoma, and in experimental autoimmune encephalomyelitis (EAE), a murine model related to multiple sclerosis.

Example I

Synthesis of NST-ML-F-4 (2-butyl-2(3-fluoropropyl)-malonic acid, NST205); (Scheme 1)

Di-t-butyl malonate (5 mL) was deprotonated with 1 eq of NaH in dimethyl formamide (DM), and 1 eq of n-butyl iodide was added after the hydrogen evolution ceased. The reaction mixture was heated to 50° C. for 14 hours. 5.8 g di-t-butyl, butyl malonate (2) were obtained in a 95% yield by using column chromatography. 2 (3.8 g) was treated with NaOCH$_3$ (0.05 eq, cat.) and acrolein (1.1 eq) in toluene to afford 1.26 g of aldehyde (3) in a 30% yield. Compound 3 was then reacted with NaBH$_4$ (1.05 eq) in a mixture of ether/water (8:1 v/v) for two hours. After work-up and flash chromatography, pure alcohol 4 was obtained (93%). The resulted product was treated with 1.1 eq of methansulfonyl chloride (MsCl) and 2.2 eq of triethyl amine (Et$_3$N) so as to obtain mesylate compound 5 in 97% yield. This product was essentially pure and directly carried over to the next reaction with no further purification.

A mixture of KF (5 eq), kryptofix (5 eq) and K$_2$CO$_3$ (2.5 eq) in 2 mL of acetonitrile was stripped to dryness under a stream of nitrogen for 4 times. The mesylate compound 5 (167 mg) in 2 mL of acetonitrile was then added. The reaction was stirred in a 120° C. sand bath for 10 min. Upon work-up, $^1$H NMR of the crude product showed a mixture of the desired product 6 and kryptofix. Deprotection of the di-t-butyl ester 6 was performed with (474 mg) and trifluoroacetic acid (TFA) (17 mL) at 10° C. for 30 min, and then evaporated to dryness. The residual material was evaporated twice from chloroform and dried on the vacuum line to afford a white solid (312 mg, 99%) of NST-ML-F-4.

NMR data of the compound are: $^1$H NMR (300 MHz, CDCl$_3$) δ 4.41 (dt, J$_t$=5.9 Hz, J$_d$=47.4 Hz, 2H), 1.97-1.91 (m, 2H), 1.89-1.83 (m, 2H), 1.69-1.60 (m, 1H), 1.58-1.52 (m, 1H), 1.33 (p, J=6.9 Hz, 2H), 1.25-1.14 (m, 2H), 0.92 (t, J=7.2 Hz, 3H); $^{13}$C NMR (75 MHz, CD$_3$OD) δ 175.8, 86.2, 84.1, 58.6, 34.1, 30.1, 30.0, 27.9, 27.3, 27.0, 24.5, 14.6; $^{19}$F NMR (282 MHz, CD$_3$OD) δ −220.9; MS (EI) m/Z 219 (M-H).

Scheme 1:

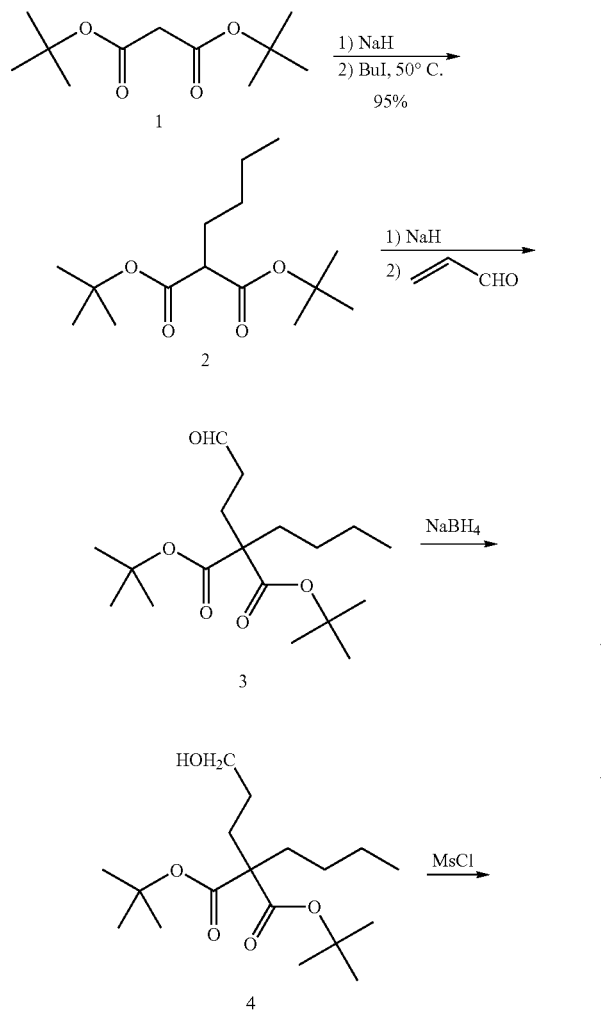

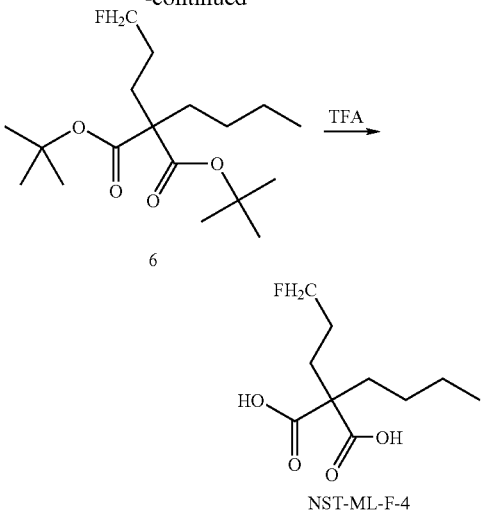

Example 2

Synthesis of NST-ML-F:
2-methyl-2(3-fluorobutyl)-malonic acid; NST201
(Scheme 2)

4-bromo-1-butanol (1), 3 g, was treated with 1.5 eq of 3,4-dihydro-2H-pyran and 0.1 eq of pyridinium para tuloenesulfonate (PPTS) in 135 mL of (CH$_2$Cl$_2$. After work-up and purification, 1.45 g (33%) of product 2 was obtained. 1.0 eq of diethylmethylmalonate was deprotonated with 1 eq of NaH and 1.0 eq of bromide 2 was added along with catalytic amount of KI at 50° C. A complete conversion was observed after 10 hours and a 90% yield was obtained. Deprotection of tetrahydro pyran (THP) with PPTS in ethanol at 55° C. went smoothly. After work-up, a quantitative yield of alcohol 4 was obtained and directly used for the mesylation reaction (as above). With the mesylate 5 in hand, the kryptofix reaction was applied as above. Compound 6 was obtained in 68% yield. Compound 6 (233 mg) was treated with 2 N NaOH/EtOH (30 mL/5 mL) at 50° C. to provide NST-ML-F ca. in 99% yield (190 mg).

The NMR data of the compound are as follows: $^1$H NMR (300 MHz, CDCl$_3$) δ 11.89 (bs, 2H), 4.46 (dt, J$_t$=5.9 Hz, J$_d$=47.2 Hz, 2H), 1.99-1.92 (m, 2H), 1.82-1.64 (m, 2H), 1.50 (s, 3H), 1.50-1.40 (m, 2H); $^{13}$C NMR (75 MHz, CDCl$_3$) δ 178.6, 85.1, 82.9, 54.2, 35.5, 31.0, 30.8, 20.8, 20.7, 20.2; $^{19}$F NMR (282 MHz, CDCl$_3$) δ −219.0; MS (EI).

Scheme 2:

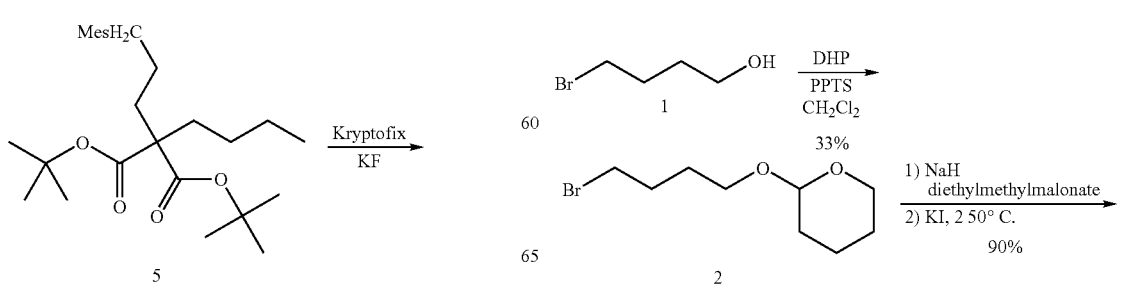

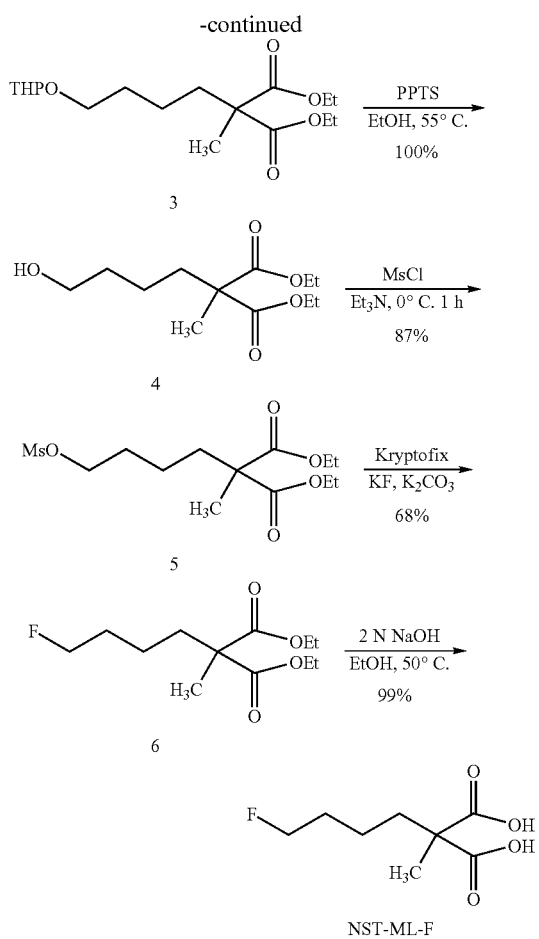

Example 3

Selective Binding of Tritium-Labeled NST 200 and NST205 to Cultured Jurkat Cells, Undergoing Apoptosis Induced by CD95

Experimental Procedure

Cultured Jurkat cells (human adult T cell leukemia cells) were grown in suspension in RPMI medium (Beit-Haemek, Israel), supplemented with 10% fetal calf serum (FCS), 2 mM of L-glutamide, 1 mM of sodium pyruvate, 1 mM HEPES and antibiotics (100 units/ml penicilin; 100 μg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with CD95 (0.1 ug/$10^7$ cells/ml). As a result, a marked percentage of the cells became apoptotic. Non-treated cells served as control. Both control cells and apoptotic cells were then incubated for 40 minutes at room temperature followed by 30 minutes on ice with (2 μCi/$10^7$ cells/ 0.5 ml) tritium-labeled NST 200 and NST 205.

After washing the cells twice, 1 ml of SOLVABLE™ reagent (GNE9100, Packard Biosciences) was added to the pellet. Following one hour of incubation at 60° C., the extracts were transferred into glass scintillation vials and 10 ml of scintillation liquid (Ultima gold 6013329, Packard Biosciences) was added to each vial. The radioactivity was counted after 1 hour of cooling to room temperature and dark adaptation. The radioactive values were calculated and presented in percents of total added radiolabeled NST 200 and NST 205

Experimental Results

Figure 2A:
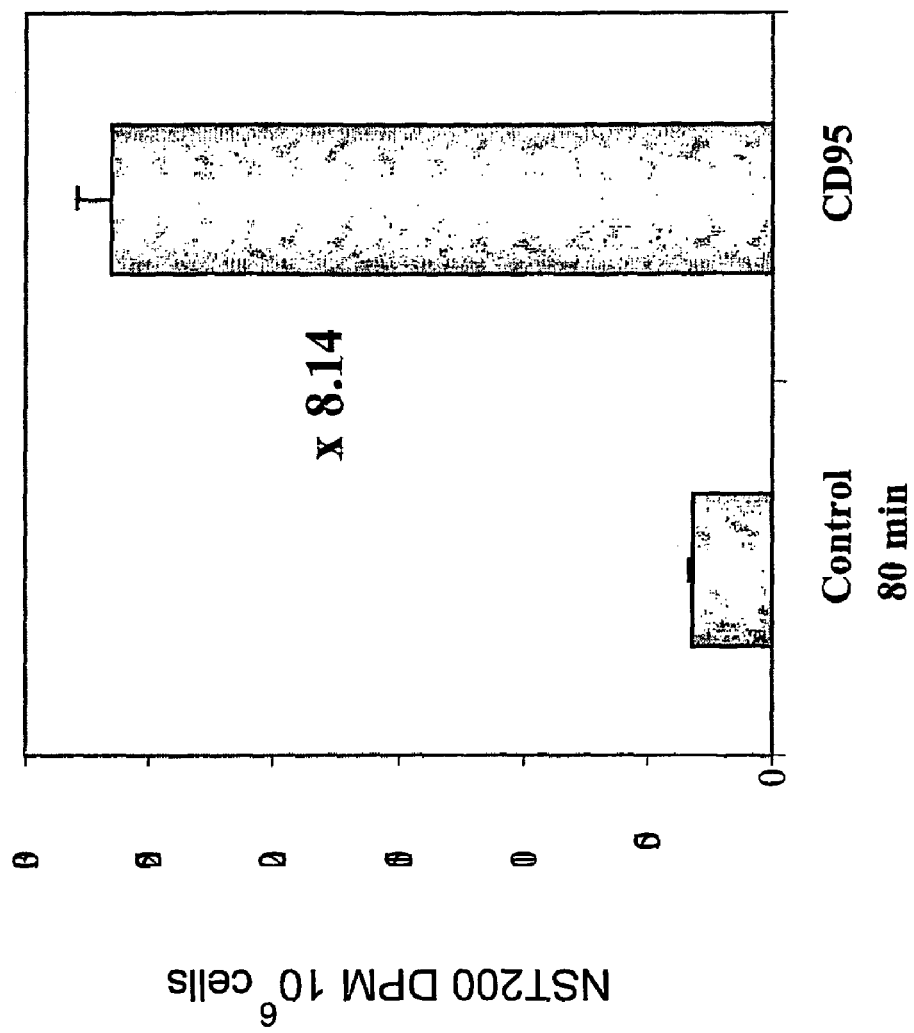
FIGS. 2 (A and B) demonstrates selective binding of tritium-labeled NST200 to cultured Jurkat cells, undergoing apoptosis induced by CD95 (A) and selective binding of tritium-labeled NST205 to cultured Jurkat cells, undergoing apoptosis induced by CD95 (B).
Figure 2B:
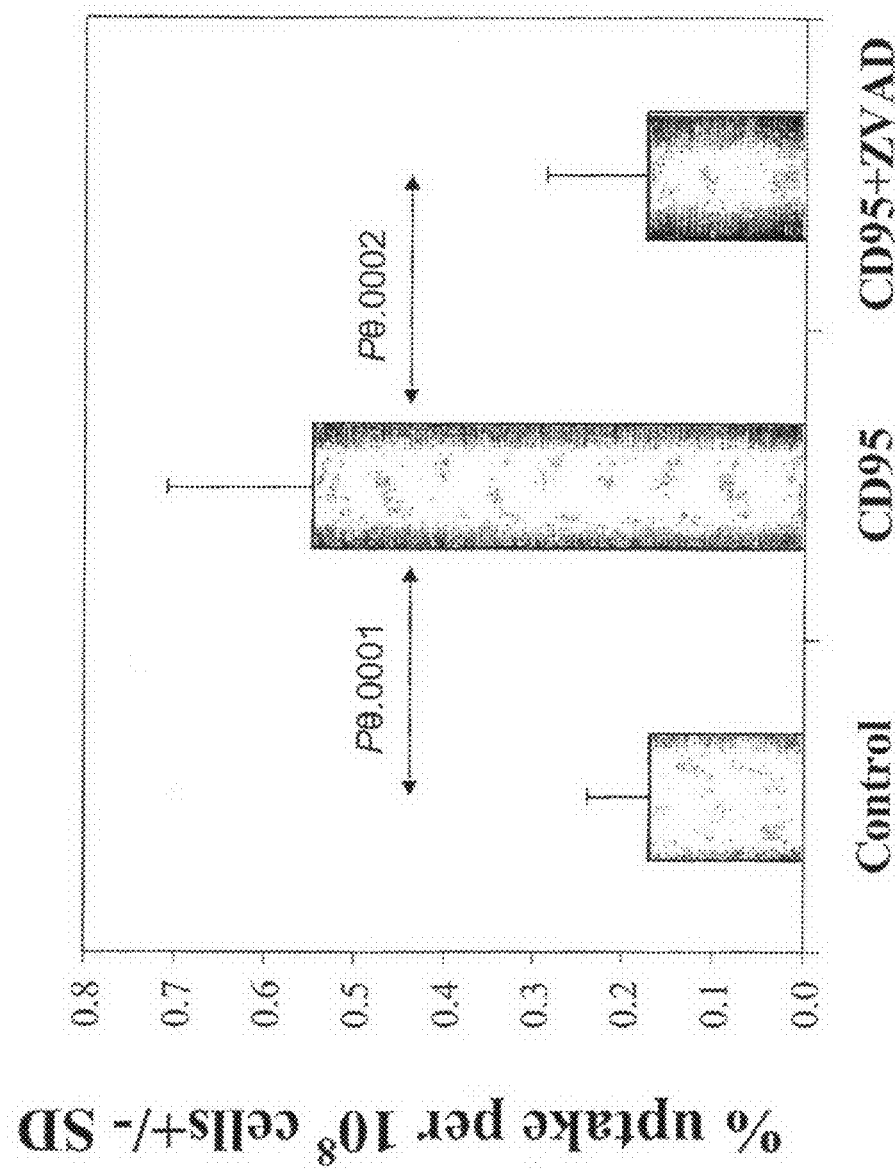

As can be clearly seen from FIG. 2A, the apoptotic cells showed markedly higher uptake of NST200 (over 8 fold) compared to the non-apoptotic cells. The experiment show that NST200 is capable of selective binding to apoptotic cells and can serve as a marker for the detection thereof. Similarly, as can be seen from FIG. 2B, the apoptotic cells showed higher uptake of NST205 in comparison to the non apoptotic cells, and this effect was completely reversed while adding ZVAD (fluoromethyl ketone peptide (V-valine, A-alanine, D-aspartate) inhibitor of caspase), which is a caspase inhibitor.

Example 4

Selective Binding of NST 203 to Cultured HeLa Cells Undergoing Apoptosis

HeLa S3 cells (ATCC CCL-2.2) were grown in Dulbecco's modified Eagle's medium (DMEM), supplemented with 2 mM of L-glutamine; 100 units/ml of penicillin; 100 μg/ml of streptomycin; 12.5 units/ml of nystatin and 10% of fetal calf serum (FCS). Cells were seeded at a density of 5×$10^6$ cells/ plate, on a 10 $cm^3$ culture plates, in a volume of 10 ml, and were allowed to age by incubating the culture for 96 hours without exchange of the growth-medium. As a result, a marked percentage of the cells became apoptotic. Cells were harvested using a cell scraper, separated to single cells by passage through a syringe with a 18 G needle, and re-suspended at a density of $10^6$ cells/ml in PBS buffer at pH=7.4. As was shown before NST 203 including a dansylamide group which enables the visualization of the fluorescence of a single cell. The selective binding of the NST203 to apoptotic cells is shown in FIG. 3A which demonstrates the uptake of NST 203 into the population of apoptotic cells (green, glowing color cells, representative are marked by arrows), while non-fluorescence is observed in the non-apoptotic cells (blue, not glowing cells, marked by arrow heads).

Figures 3A, 3B:
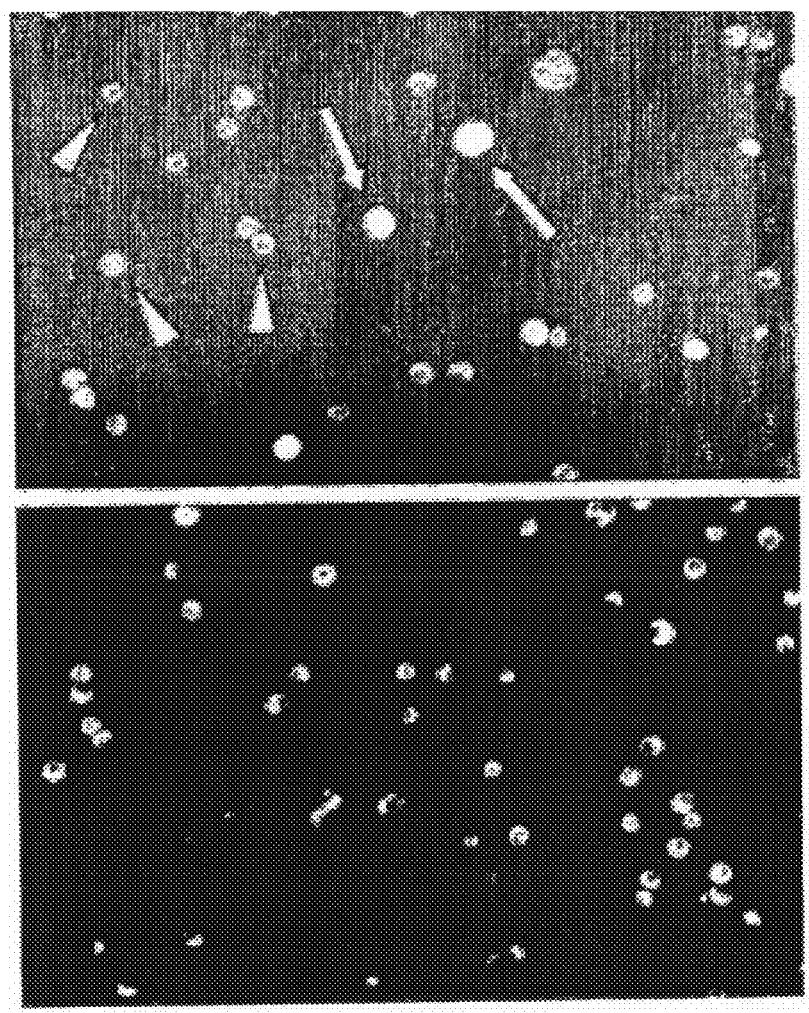
FIGS. 3 (A and B) shows fluorescent microscopy, demonstrating the selective binding of NST203 to cultured HeLa cells undergoing apoptosis (FIG. 3A). The control compound, n-butyl-dansylamide (BDA), having the same fluorophore but devoid of the NST-ML-Action Motif, did not manifest this selectivity (FIG. 3B).

By contrast, the control compound n-butyl-dansylamide (BDA), having the same fluorophore but devoid of the NST-ML-Action Motif, did not manifest this selectivity, thus manifesting the activity of the NST-ML-Action Motif in selective binding to the apoptotic cells (FIG. 3B). Therefore, NST203 can serve as a marker, which performs selective binding to apoptotic cells.

Example 5

Selective Binding of NST 203 to Melanoma Cells Undergoing a Death Process Induced by Chemotherapy in Mice In Vivo

Experimental Procedure

Mice (c57/black; 8 weeks old male mice) were injected subcutaneously bilaterally, in the flank, with murine melanoma-derived B16-F10 cells (ATCC CRL-6475; $10^5$ cells/ mice in a volume of 100 μl). Prior to injection, the cell line was maintained in culture in Dulbecco's modified Eagle's medium (DMEM), supplemented with 4 mM of L-glutamine; 100 units/ml of penicillin; 100 μg/ml of streptomycin; 12.5 units/ml of nystatin and 10% of fetal calf serum (FCS). After 10 days, when tumor diameter reached the size of 5-7 mm, mice were subjected to chemotherapy treatment (Taxol 20 mg/Kg together with Cyclophosphomide, 300 mg/Kg, in a volume of 200 μl intra-peritoneal injection). Twenty-four hours later, NST-203 was injected intravenously, at a dose of 2.8 mg/mouse in 10% chromophore in tris-base buffer. Two hours later, mice were sacrificed and tumors as well as other organs were harvested and immediately frozen in liquid nitrogen. Uptalke of NST-203 by the tumors or other organs was assessed by fluorescent microscopy of frozen sections from each tissue.

Experimental Results

Figure 4A:
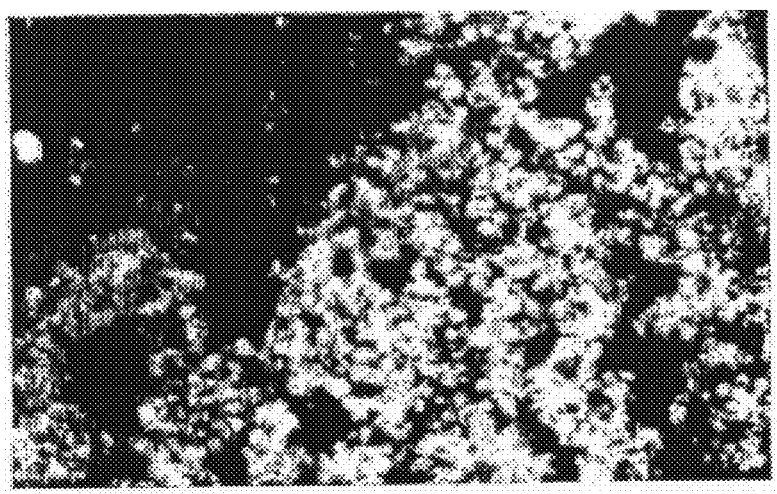
FIGS. 4 (A and B) shows fluorescent microscopy of the selective binding of NST203 to cells undergoing cell death induced by chemotherapy in mice in vivo: (A.). Apoptosis of melanoma cells; (B). Apoptosis of epithelial cells of the gastrointestinal tract.

FIG. 4A shows fluorescent microscopy of the tumor. Extensive binding of NST203 to numerous tumor cells undergoing apoptosis can be observed. Demonstrated are also the intracellular accumulation of the compound (right side of the picture) and the high level of selectivity, reflected by a marked uptake into the apoptotic cells, while the surrounding viable tumor cells remain unstained (left upper side of the picture).

Figure 4B:
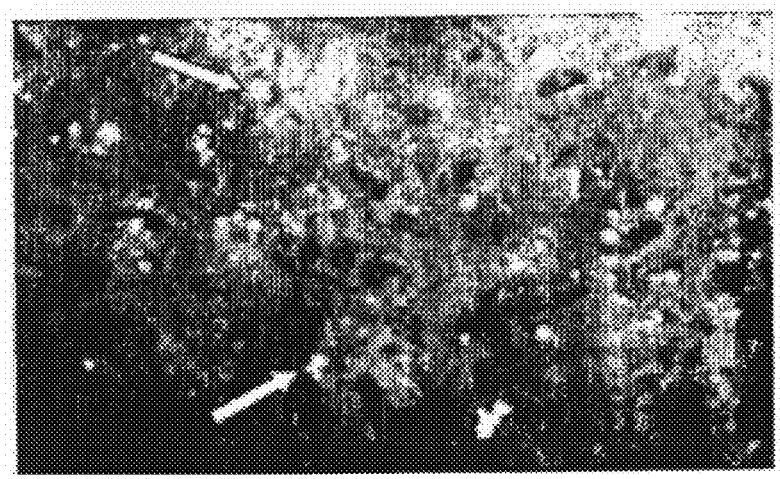

Chemotherapy often acts to induce cell death no only in target tumor tissue, but also in non-target tissues, such as the epithelium of the gastrointestinal tract. FIG. 4B shows the capability of NST203 to selectively detect these cells undergoing apoptosis (see arrows). Similar to the findings in the tumor, viable cells in the gastrointestinal tract did not manifest uptake of NST203 and therefore remained dark.

These results therefore manifest the capability of the compound of the invention, NST203, to target specifically apoptotic cells in vivo, wherein the death process is being induced by chemotherapy. The apoptotic cells are detected in a universal manner, irrespective of the tissue involved. By contrast, viable cells of said tissues do not manifest such binding.

Example 6

Imaging, by Autoradiographic Methods with $^3$H-NST200, of Response to Chemotherapy in a Mouse Model of Colon Carcinoma Experimental Procedure Colon carcinoma model was established in the abdomen of Balb/c male mice. At day 12-14 when tumor size was 6-8 nm n in diameter, the uptake of NST200 into tumors was measured following treatment of colon carcinoma tumors with i.v. injection of two doses of doxorubicin (20 mg/kg, 72 hours apart). Fourty-eight hours after the chemotherapy, both the control non-treated and the chemotherapy-treated animals were injected intravenously with and radio-labeled NST200 (80 μCi/animal) Four hours later, the animals were sacrificed. 10 μm frozen sections were prepared, air-dried and exposed to a tritium sensitive film. The film was exposed for a duration of 7 weeks, developed and analyzed by densitometny measurement. Measurement of $^3$H-DDC densities in optical density/mm$^2$, in the ischemic core vs. the contralateral hemisphere signal was assessed by TINA software. Signals were translated according to a Microscale autoradiography standards and expressed in nCi/mg units.

Experimental Results

Non-treated tumors exhibit no uptake of NST200, and therefore, no image could be detected by autoradiography (FIG. 5A). However, upon induction of cell death via chemotherapy, a dramatic increase in NST 200 uptake occurs indicating a massive process of irradiation-induced cell death. (FIGS. 5 B and C)

NST 200 uptake can be detected at multiple foci on the surface of the tumors in the form of dark intense patches. NST-200 labeling localized to specific foci of apoptotic areas within the tumor and was not diffused throughout the tumor. Other areas of the treated tumors were not labeled, indicative of vital tumor tissue. This observation emphasized the advantage of NST 200 as targeting molecule that is accumulating selectively in large quantities in dying and not in live cells (FIG. 5B). The heterogeneous nature of response to therapy even within the same tumor is manifested in FIG. 5C: the uptake of NST200 accumulates especially in one large area of the tumor that was exhibited increased cell death, but not in other tumor areas, that did not response to the chemotherapy Example 7

Uptake of 3H-NST 200 into Colon Carcinoma Model: Effect of Chemotherapy

Experimental Procedure

Colon Carcinoma Model

Murine colon carcinoma cells (CT-26) (ATCC CRL-2638) were maintained in RPMI (Gibco, UK), 2 mM of L-glutamine; 100 units/ml of penicillin; 100 μg/ml of streptomycine; 12.5 units/ml nystatin; and 10% heated inactivation FCS. Studies were carried out in adult male Balb/C mice 8-10 weeks old (weighting 20-25gr).

Inoculation of Tumor:

Cells were trypsinized, washed twice with HBS (140 mM NaCl; 0.5M Hepes, PH 7.4) and than centrifuged (5 min, 1000 rpm, 4° C.) and concentrated into $2\times10^6$ cells/ml in a mixture of (2%) methyl cellulose and saline (1:3). A volume of 0.2 ml of the above solution (containing $4\times10^5$ cells/dose) was injected subcutaneously into the mice abdomen in both sides while mice were anaesthetized. Anaesthetic stock solution was prepared from 0.85 ml Ketamine (100 mg/ml)+0.15 ml Xilazine (2%) diluted 1:10. 0.1 ml of diluted solution was injected (i.p.) per 10 gr body weight.

Tumor Follow Up:

Mice were examined daily for palpable tumor formation. 7-10 days after tumor injection small tumors were visible.

Evaluation of $^3$H-NST200 Uptake into Colon Carcinoma Tumors

Uptake of $^3$H-NST200 into tumors was measured following treatment of colon carcinoma tumors with i.v. injection of two doses of doxorubicin (20 mg/kg, 72 hours apart). 48 hours after the second dose, the mice were intravenously injected with $^3$H-NST200 (10 μCi/animal). Four hours later, tumors were collected, weighed and the tissue was processed: tumor lysis was performed using SOLVABLE™ reagent (GNE9100, Packard Bioscience) in a ratio of one ml reagent per 150 mg of tumor tissue at 60° C. in 20 ml scintillation glass vials. Following 2-4 hours, one ml from each tissue extract was transferred to a glass scintillation vial. To reduce color quenching problems, samples were treated with 0.4 ml of 30% $H_2O_2$ in the presence of 0.066M EDTA. After 15 min of incubation time at room temperature, extracts were incubated for 1 hr at 60° C., followed by further 15 min incubation at room temperature. Ten (10) ml of scintillation liquid (Ultima gold, 6013329, Packard Bioscience) was added to each vial. The vials were incubated for 1 hr at RT, and than analyzed in a β-counter (TRI-CARB 2100TR, liquid scintillation analyzer, Packard Bioscience). All samples were measured in triplicates Values of percents of injected dose (% ID/g tissue) were calculated for each sample.

Experimental Results

Figure 6:
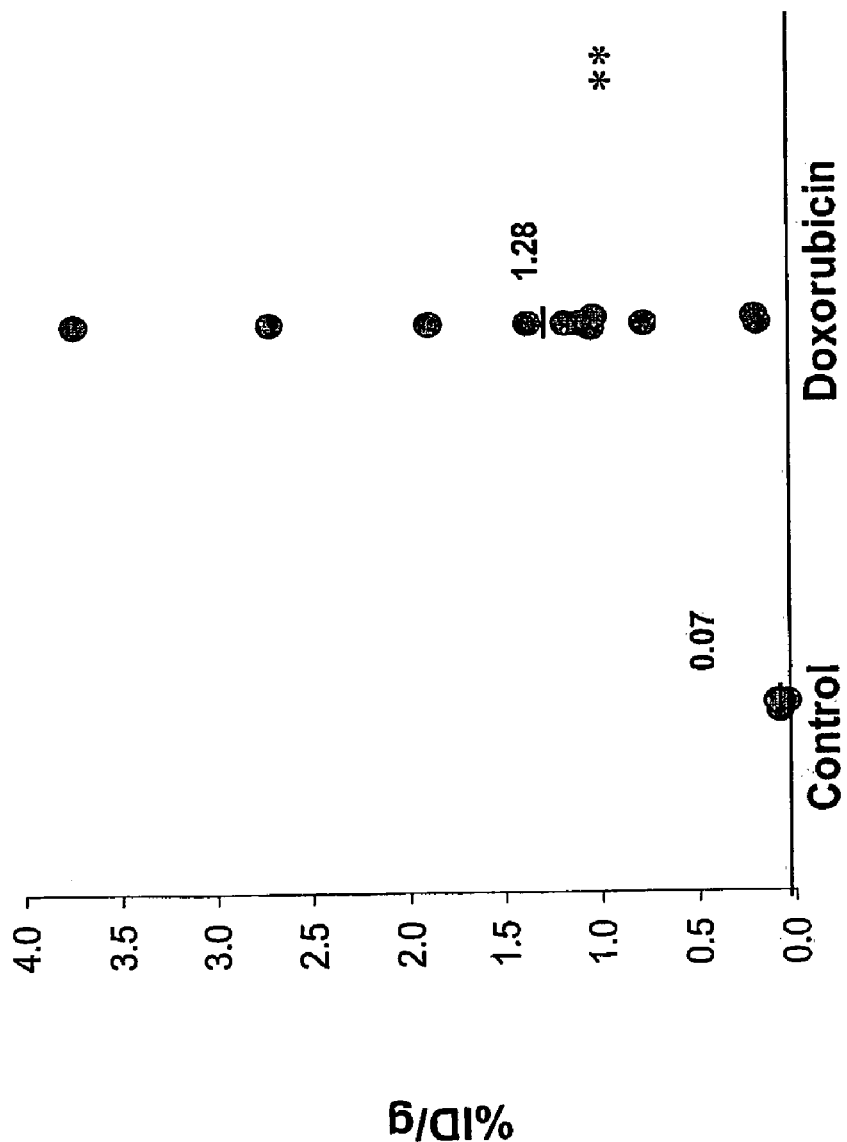
FIG. 6 shows autoradiography by NST 200 in chemotherapy treated mice with colon carcinoma.

The quantitative analyses of $^3$H-NST200 accumulation in doxorubicin treated colon carcinoma tumors versus non treated control tumors revealed a massive accumulation of $^3$H-NST200 at 48 hr following treatment. While in control group all tumors accumulated similar and low amounts of $^3$H-NST200, in the chemotherapy-treated tumors the accumulation values were variable with some tumors that exhibited a 40-50 fold increase in uptake as compared with the control group. The mean value of uptake in the treated group was 1.28% ID/gr, which is 12.1 fold more than the mean value of the control group (see FIG. 6).

The wide spectrum of $^3$H-NST200 accumulated values, reflects the individual response of different tumors to the anti cancer treatment. The above experiment clearly shows that $^3$H-NST200 can serve for detecting carcinoma and the for detecting the effect of cytotoxic drugs on the carcinoma cells.

Example 8

Biodistribution of $^3$H-NST200 in Colon Carcinoma Tumor Bearing Mice

Experimental Procedure

Colon carcinoma model was established in the abdomen of Balb/c male mice, as described in previous example, and $^3$H-NST200 (10 μCi) was injected to animals treated with doxorubicin. Four hours later, the animals were sacrificed and various organs/tissues were collected and processed, to determine the accumulation of $^3$H-NST200 within them. The uptake in each organ was expressed as % of the injected dose (ID), and the ratio between the uptake in the tumor and other organs was calculated, as shown in the table attached hereto as FIG. 7.

Experimental Results

The damage induced by doxorubicin to tumor tissue indeed exceeded the damage to other non-target organs, including the heart and the small intestine. The ratio of uptake in the tumor vs. all organs in the table is >1, showing increased apoptosis in the tumor and selective accumulation of $^3$H-NST200 in the target vs. non-target tissues.

Example 9

$^3$H-NST200 can Detect Cell Death Occurring within BiCNU-Treated Tumors, Before Shrinkage of Tumor Size Experimental Procedures Colon carcinoma model was established in the abdomen of Balb/c male mice, as described in Example No. 10. At day 12-14 when tumor size was 6-8 mm in diameter, mice were injected intravenously with doxorubicin. A total of 2 doses of doxorubicin were given, separated by 3 days interval (each dose was 20 mg/Kg).

Two days after the second doxorubicin injection, mice were injected i.v. with 10 μCi of $^3$H-NST200 in a volume of 0.2 ml saline. Four hours following $^3$H-NST200 injection, mice were sacrificed by pental overdosing. Tumors were collected in ependorff tubes, weighted and frozen in −20° C.

Tumor lysis was performed using SOLVABLE™ reagent (GNE9100, Packard Bioscience) in a ratio of 1 ml reagent per 150 mg of tumor tissue at 60° C. in 20 ml scintillation glass vials. Following 2-4 hours, 1 ml from each tissue extract was transferred to a glass scintillation vial. To reduce color quenching problems, samples were treated with 0.4 ml of 30% $H_2O_2$ in the presence of 0.066M EDTA. After 15 min of incubation time at room temperature, extracts were incubated for 1 hr at 60° C., followed by further 15 min incubation at room temperature. Ten (10) ml of scintillation liquid (Ultima gold, 6013329, Packard Bioscience) was added to each vial. The vials were incubated for 1 hr at RT, and than analyzed in a β-counter (TRI-CARB 2100TR, liquid scintillation analyzer, Packard Bioscience). Values of percents of injected dose (% ID/g tissue) were calculated for each sample. Comparison between NST200 uptake and tumor volume is shown. The uptake values of NST200 after each dose were correlated with tumor volume, which were calculated by the formula (assuming spherical tumors) $V=\pi D^3/6$, where D is the average tumor diameter.

Experimental Results

Figures 8A, 8B:
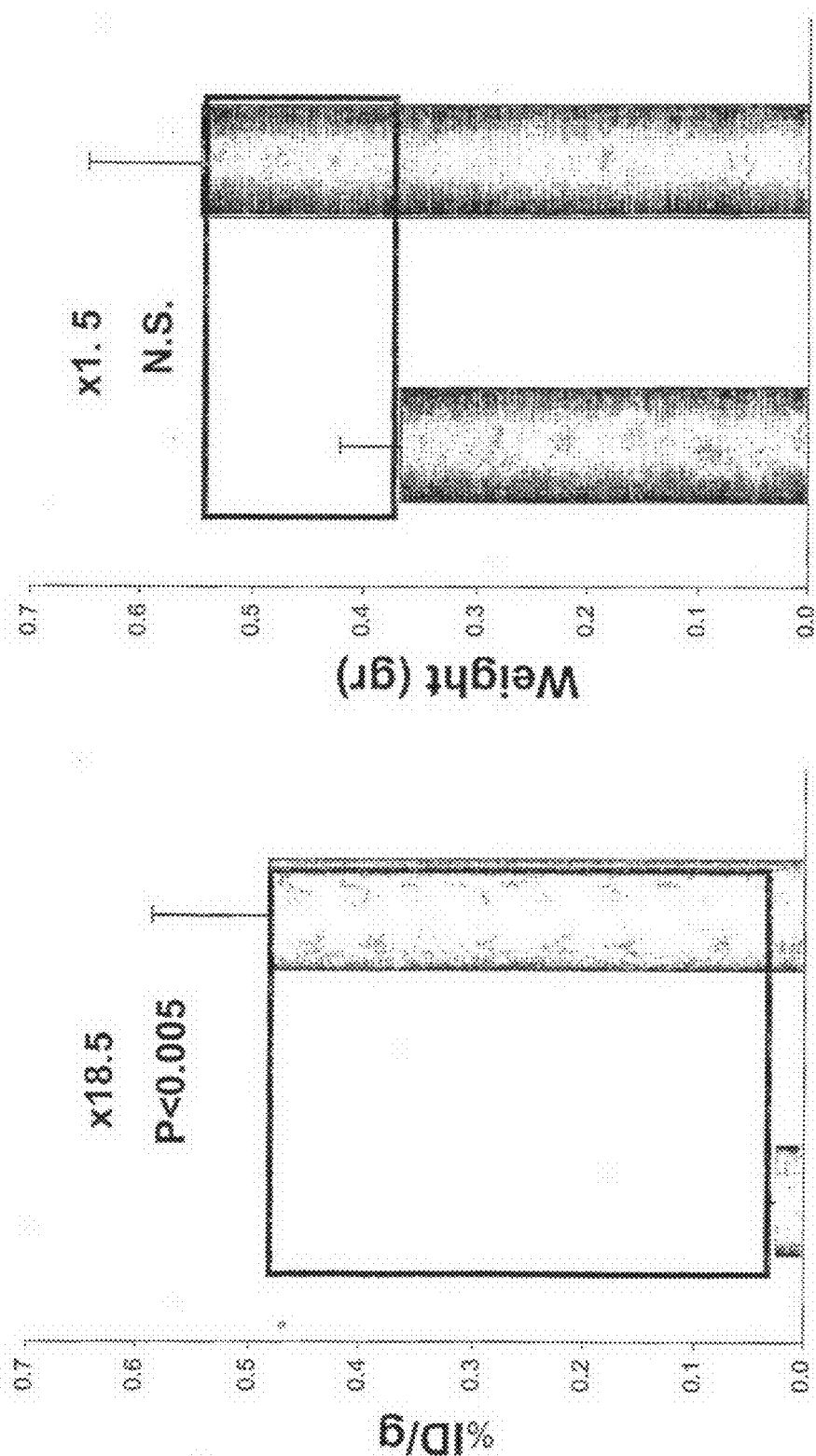
FIG. 8B demonstrates changes in the colon weight.

During the treatment with doxorubicin (lasting 5 days), the tumor mass was not reduced (see FIG. 8A). In contrast, the tumor continued to grow, exhibiting a 50% increase in their volume, as compared to the control non-treated tumors, that were collected 5 days earlier than the treated tumors. This increase was found to be non-significant. While such non-significant change in tumor volume occurred after 2 doses of doxorubicin treatment, a dramatic increase, by 18.5 fold in $^3$H-NST200 uptake was detected, indicating that $^3$H-NST200 is a sensitive tool, capable of sensing cell death within the tumor even in cases where no shrinkage of tumor mass is detected (see FIG. 8B).

Example 10

Use of Tritium-Labeled NST200 for the Detection, by Autoradiography Methods, of Apoptotic Damage Following Middle Cerebral Artery Occlusion in Mice Experimental Procedure p-MCA was induced through a subtemporal approach in Balb/C mice with an outcome of a pronounced ischemic damage. Twenty-two hours after p-MCA, the animal's neurological score was assessed (from 0-no clinical signs to 3-hemiplegia, circling and catatonia) and radio-labeled NST200 (80 μCi/animal) was intravenously injected for successive 2 h before sacrificing the animals. 10 μm frozen sections were prepared, air-dried and exposed to a tritium sensitive film (Hyperfilm-3h, RPN535B Amersharn-Pharmacia, Eu). The film was exposed for a duration of 7 weeks, developed (GBX Developer & Fixer, Kodak, USA) and analyzed by densitometry measurement. Measurement of $^3$H-DDC densities in optical density/mm$^2$, in the ischemic core vs. the contralateral hemisphere signal was assessed by TINA software. Signals were translated according to a Microscale autoradiography standards (RPN510 Amersham-Pharmacia, Eu) and expressed in nCi/mg units.

Experimental Results

Figure 9B:
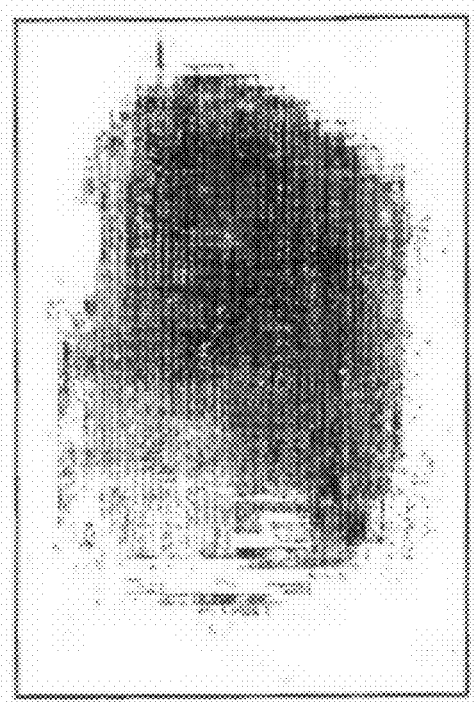
FIGS. 9 (A and B) demonstrates autoradiographic image analysis showing targeting of tritium-labeled NST200 to region of apoptotic death in the brain (A) and H&E staining (B).
Figure 9A:
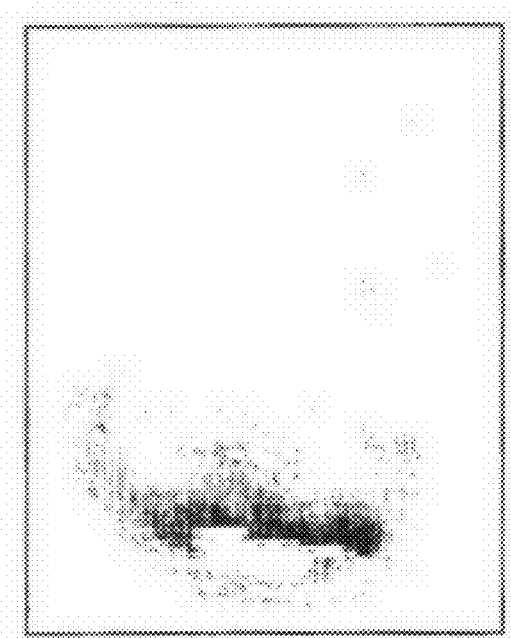

As can be seen from FIG. 9, which shows accumulation of $^3$H-NST 200 (a) and H&E staining (b), autoradiographic image analysis revealed the specificity of targeting the injury by $^3$H-NST200 within the regions of apoptotic/necrotic cell death. The results were further confirmed by H& E staining. Accordingly, $^3$H-NST200 can be used as a marker for brain apoptotic damage in autoradiographic image analysis.

Example 11

Autoradiography by 31-Radiolabeled NST 200 of Rat Renal Ischemia-Reperfusion (I/R)

Experimental Procedure

Operative procedures were performed in rats under general anesthesia induced by the combination of Ketamine (80 mg/kg) and Xylazine, (10 mg/kg), administrated intraperitoneally. Renal ischemia was induced by unilateral left renal artery clamping, using a small nontraumatic vascular clamp, for 45 minutes. The contralateral, untreated kidney from the same animal was designed as kidney from sham-operated control. Reperfusion was initiated by removal of the clamp. Period of renal reperfusion was 24 hours. During the course of reperfusion, animals were injected intravenously with 100 μCi of $^3$H-NST205 and one hour later, both kidneys were excised, frozen in liquid nitrogen, and stored at –70° C. until use. 10 μm frozen sections were prepared, air-dried and exposed to a tritium sensitive film (Hyperfilm-3h, RPN535B Amersham-Pharmacia, Eu). The film was exposed for a duration of 7 weeks, developed (GBX Developer & Fixer, Kodak, USA) and analyzed by densitometry measurement. Measurement of $^3$H-DDC densities in optical density/mm$^2$, in the ischemic kidney vs. the contralateral kidney signal was assessed by TINA software. Signals were translated than according to Microscale autoradiography standards (RPN510 Amersham-Pharmacia, Eu) and expressed in nCi/mg units.

Experimental Results

As shown in FIG. 10, during ischemia-reperfusion injury in the rat kidney, apoptosis was observed in the distal tubules of the cortico-medullary region and outer medulla (OM) while severe necrosis was seen in the proximal straight tubules of the (OM). Less damage was observed in the cortex. No damaged tubules in the contralateral, sham kidney were observed. Autoradiographic image analysis revealed the specificity of targeting the injury by $^3$H-NST205 within the regions of apoptotic/necrotic cell death, confirmed by morphological analysis. By contrast, no $^3$H-NST205 uptake into contralateral kidney was demonstrated, emphasizing the specificity of $^3$H-NST205 uptake only into the injured kidney.

Example 12

Autoradiography by 3H NST205 in a Rat Model of Radiocontrast-Induced Acute Distal Tubular Necrosis (ATN)

Experimental Procedures

Nephropathy with selective medullary hypoxic tubular damage was induced by the combined administration of indomethacin (Sigma Chemical Co.), 10 mg/kg, i.v., N$^\omega$nitro-L-arginine methyl ester (L-NAME, Sigma Chemical Co.), 10 mg/kg, i.v., and radiocontrast agent sodium-iothalamate 80% (Angio-Conray, Mallinckrodt Inc), 6 mL/kg, i.a. Additional rats injected with vehicles served as control. Twenty-four hours after insult, animals, both control and experimental were intravenously injected with 100 μCi of $^3$H-NST205 and one hour later kidneys were excised and frozen in liquid nitrogen.

Experimental Results

As can be seen from FIG. 11, renal morphology analysis disclosed wide-ranging extent of medullary (namely, outer and inner strip of outer medulla) damage. Homing of $^3$H-NST205 was primarily restricted to injured regions within the outer medulla. There was no observation of $^3$H-NST205 uptake at a specified region in the absence of morphologic damage.

Example 13

Imaging of Experimental Autoimmune Encephalomyelitis (EAE) by $^3$H-200; Autoradiography Experimental Procedure EAE was induced by immunization of C3H.SW/C57/bl female mice, 6-8 week-old. The animals were immunized with the peptide encompassing amino acids 35-55 of rat myelin oligodendrocyte glycoprotein (MOG). The peptide was synthesized using a solid-phase technique on a peptide synthesizer. Mice were injected subcutaneously at one site in a flank with a 200 μl emulsion containing 75 μl MOG peptide in complete Freund's adjuvant (CFA) and 200 μg *mycobacterium tuberculosis*. An identical buster was injected at one site in the other flank 1 week later. Following the encephalitogenic challenge mice were observed daily and clinical manifestation of EAE were scored (from 0=no clinical signs to 5=total paralysis of four limbs). At a selected stage of the disease (Pre-symptoms or end-stage) animals were intravenously injected with radio-labeled NST200 (100 μCi/animal) for one hour of incubation before sacrificing the animals. 10 μm frozen sections were prepared, air-dried and exposed to a tritium sensitive film. The film was exposed for duration of 7-9 weeks, developed and analyzed by densitometey measurement. Measurement of $^3$H-DDC densities in optical density/mm$^2$, in the ischemic core vs. the contralateral hemisphere signal was assessed by TINA software.

Experimental Results

Figure 12:
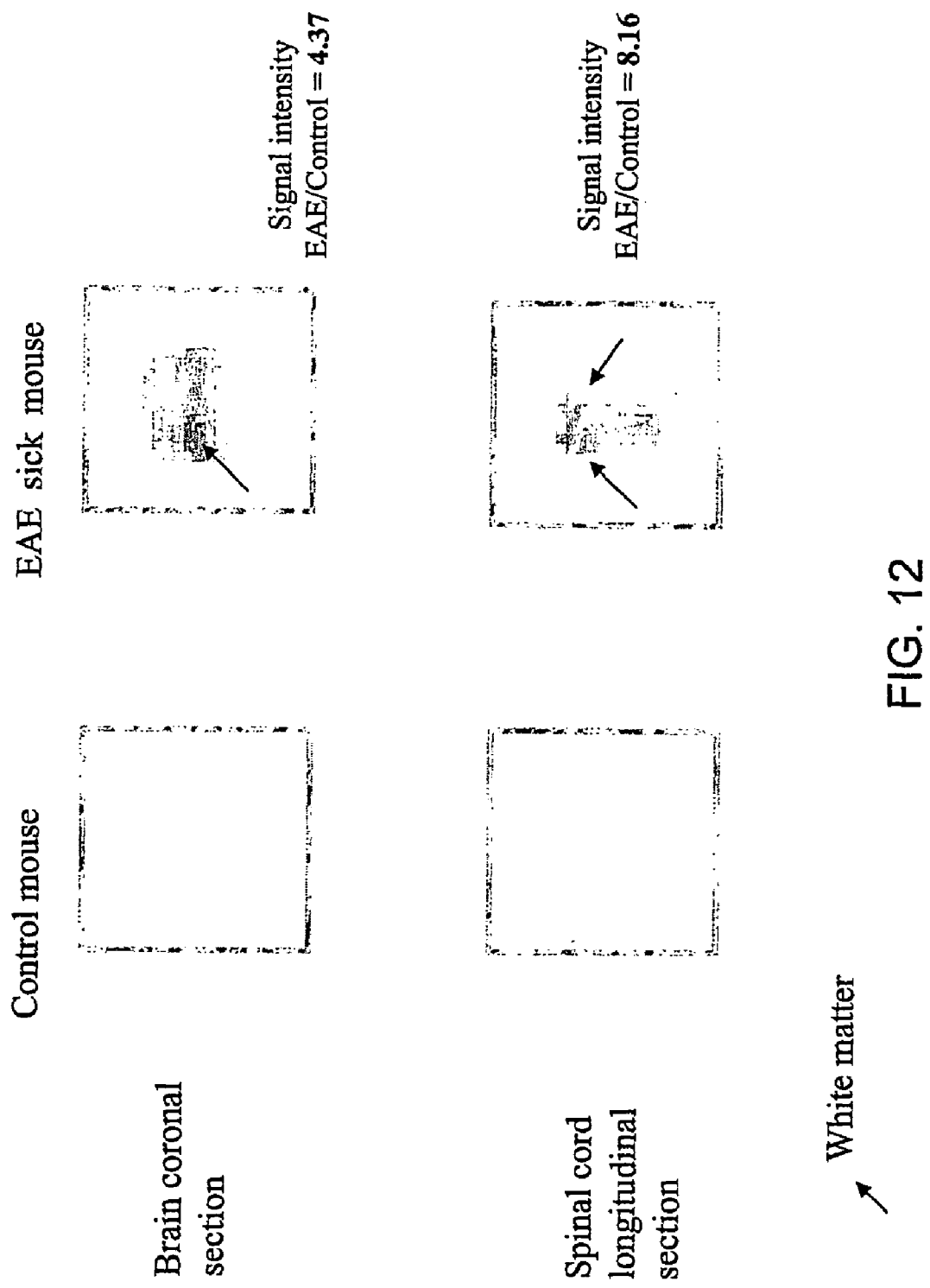
FIG. 12 shows $^3$H-200 imaging by autoradiography in brain and spinal cord of Experimental Autoimmune Encephalomyelitis.

The EAE animal model of multiple sclerosis disease mimicked the chronic disabling autoimmune neurological disorder targeting the white matter of the central nerve system. The severe damage of the white matter in the experimental animals was observed in the autoradiography demonstrated in FIG. 12. At the brain level, the coronal sections expressed a dark staining of the pyramidal tracts at the bottom of the brain and an excess of radio-ligand accumulation in the whole brain in comparison to the bright staining of the control, non-immunized mouse. An impressive accumulation of the radio labeled $^3$H-200 was observed also at the spinal cord level. A longitudinal section of the spinal cords presented a high level of labeling of the lateral tracts of the white matter in the immunized mouse, compared to the spinal cord of the control untreated animal.

The invention claimed is:

1. A compound represented by the structure as set forth in formula II,

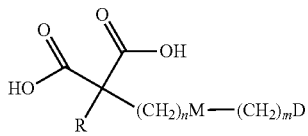

including pharmaceutically acceptable salts, hydrates, solvates and metal chelates of the compound represented by the structure as set forth in formula (II) and solvates and hydrates of the salts; wherein R represents hydrogen or $C_1, C_2, C_3, C_4, C_5, C_6, C_7, C_8, C_9, C_{10}, C_{11}, C_{12}, C_{13}, C_{14}, C_{15}$ or $C_{16}$ linear or branched alkyl; n and m each stands independently for an integer of 0, 1, 2, 3 or 4; n and m may be same or different; M is selected from null, —O—, —S— and —N(U), wherein U stands for hydrogen, $C_1, C_2, C_3$, or $C_4$ alkyl; and D is a marker for diagnostics, or a drug to be targeted to PNOM-cells.

2. The compound according to claim 1, wherein M is null.

3. The compound according to claim 1, represented by the structure as set forth in formula (III):

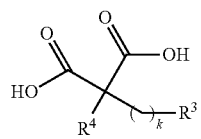

including pharmaceutically acceptable salts, hydrates, solvates and metal chelates of the compound represented by the structure as set forth in formula (III) and solvates and hydrates of the salts; wherein $R^3$ is $^{18}F$, $R^4$ is selected from $C_4, C_5, C_6, C_7, C_8, C_9$ or $C_{10}$ linear or branched alkyl, and k is an integer selected from 0, 1, 2, 3, 4 and 5.

4. The compound according to claim 1, represented by the structure as set forth in formula (V):

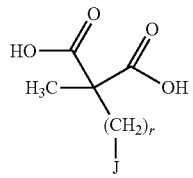

including pharmaceutically acceptable salts, hydrates, solvates and metal chelates of the compound represented by the structure as set forth in formula (V) and solvates and hydrates of the salts; wherein J is $^{18}F$, and r stands for an integer of 4, 5, 6, 7 or 8.

5. The compound according to claim 4, wherein r is 5 and J is $^{18}F$.

6. The compound according to claim 4, wherein r is 4 and 3 is $^{18}F$.

7. The compound according to claim 1, represented by the structure as set forth in formula (VI):

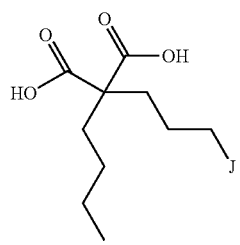

including pharmaceutically acceptable salts, hydrates, solvates and metal chelates of the compound represented by the structure as set forth in formula (VI) and solvates and hydrates of said salts; wherein J is $^{18}F$.

8. The compound according to claim 1, represented by the structure set forth in formula (IX):

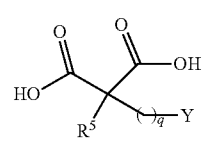

including pharmaceutically acceptable salts, hydrates, solvates and metal chelates of the compound represented by the structure as set forth in formula (IX) and solvates and hydrates of said salts; wherein $R^5$ is selected from hydrogen, $C_1, C_2, C_3, C_4, C_5$, or $C_6$ linear or branched alkyl; q stands for an integer selected from 1, 2, 3, 4 and 5; and Y is a marker for diagnostics comprising a NH-dansyl and fluorescent.

9. The compound according to claim 8, wherein $R^5$ is $CH_3$; and q is selected from 3, 4, and 5.

10. The compound according to claim 8, represented by the structure as set forth in formula (X):

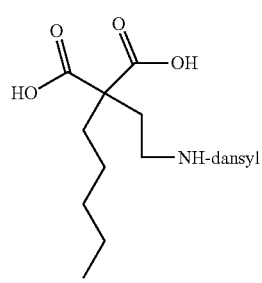

including pharmaceutically acceptable salts, hydrates, solvates and metal chelates of the compound represented by the structure as set forth in formula (X) and solvates and hydrates of said salts.

11. The compound according to claim 1, represented by the structure as set forth in formula (XI):

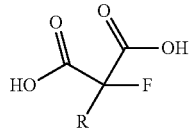

XI including pharmaceutically acceptable salts, hydrates, solvates and metal chelates of the compound represented by the structure as set forth in formula (XI) and solvates and hydrates of the salts; wherein R represents hydrogen or $C_1$, $C_2$, $C_3$, $C_4$, $C_5$, $C_5$, $C_7$, $C_8$, $C_9$ $C_{10}$, linear or branched alkyl, wherein F is $^{18}$F or $^{19}$F.

12. The compound according to claim 1, represented by the structure set forth in formula XIII:

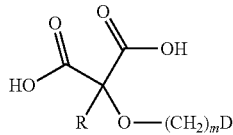

XIII including pharmaceutically acceptable salts hydrates, solvates and metal chelates of the compound represented by the structure as set forth in formula (XIII) and solvates and hydrates of the salts; wherein R represents hydrogen or $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$ or $C_{16}$ linear or branched alkyl, m stands for an integer of 0, 1, 2, 3 or 4; D is a marker for diagnostics or a drug to be targeted to PNOM-cells.

13. The compound according to claim 12, wherein R represents hydrogen or $C_1$, $C_2$, $C_3$, $C_4$, $C_5$, $C_6$, $C_7$, $C_8$, $C_9$ or $C_{10}$ linear or branched alkyl; m is 2 and D is $^{18}$F.

14. The compound according to claim 12, represented by the structure set forth in formula (XIV):

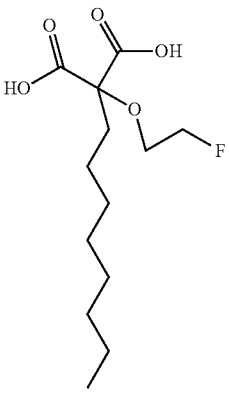

XIV including pharmaceutically acceptable salts, hydrates, solvates and metal chelates, of the compound represented by the structure as set forth in formula (XIV) and solvates and hydrates of the salts; wherein F is $^{18}$F.

15. The compound of according to claim 1, wherein said marker for diagnostics comprises Tc, Tc=O, In, Cu, Ga, Xe, Tl, Re and Re=O, $^{123}$I, $^{131}$I, Gd(III), Fe(III), $Fe_2O_3$, $Fe_3O_4$, Mn(II) $^{18}$F, $^{15}$O, $^{18}$O, $^{11}$C, $^{13}$C, $^{124}$I, $^{13}$N, $^{75}$Br, Tc-99m or In-111.

16. The compound according to claim 1, wherein said marker for diagnostics is detectable by a detector of color, fluorescence, x-ray, CT scan, magnetic resonance imaging (MRI), radio-isotope scan, single photon emission tomography (SPECT) or positron emission tomography (PET).

17. The compound according to the structure set forth in any one of claims 1, 3, 4, 7, 8, 10, 11, 12, or 14, comprising or being linked to a marker for imaging.

18. The compound according to claim 17, wherein said marker is Tc, Tc=O, In, Cu, Ga, Xe, Tl, Re and Re=O, $^{123}$I, $^{131}$I, Gd(III), Fe(III), $Fe_2O_3$, $Fe_3O_4$, Mn(II) $^{18}$F, $^{15}$O, $^{18}$O, $^{11}$C, $^{13}$C, $^{124}$I, $^{13}$N, $^{75}$Br, Tc-99m or In-111.

19. The compound according to claim 17, wherein said marker for imaging is detectable by a detector of color, fluorescence, x-ray, CT scan, magnetic resonance imaging (MRI), radio-isotope scan, single photon emission tomography (SPECT) or positron emission tomography (PET).

* * * * *

UNITED STATES PATENT AND TRADEMARK OFFICE
CERTIFICATE OF CORRECTION

| | | |
|---|---|---|
| PATENT NO. | : 7,947,253 B2 | Page 1 of 1 |
| APPLICATION NO. | : 10/585928 | |
| DATED | : May 24, 2011 | |
| INVENTOR(S) | : Ilan Ziv et al. | |

It is certified that error appears in the above-identified patent and that said Letters Patent is hereby corrected as shown below:

Col. 37, line 66, should read:

"6. The compound according to claim 4, wherein r is 4 and [[3]] J is $^{18}$F"

Signed and Sealed this
Fourth Day of October, 2011

David J. Kappos
*Director of the United States Patent and Trademark Office*